United States Patent
Zhang et al.

(10) Patent No.: US 9,714,941 B2
(45) Date of Patent: Jul. 25, 2017

(54) BIO-SENSING NANODEVICE

(75) Inventors: Shuguang Zhang, Lexington, MA (US); Andreas Mershin, Cambridge, MA (US); Liselotte Kaiser, Stockholm (SE); Brian Cook, Somerville, MA (US); Johanna F. Graveland-Bikker, Lexmond (NL); Manu Prakash, Cambridge, MA (US); David Kong, Lexington, MA (US); Yael Maguire, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 2214 days.

(21) Appl. No.: 12/183,916

(22) Filed: Jul. 31, 2008

(65) Prior Publication Data
US 2009/0156427 A1    Jun. 18, 2009

Related U.S. Application Data

(60) Provisional application No. 60/953,030, filed on Jul. 31, 2007.

(51) Int. Cl.
*G01N 33/543* (2006.01)

(52) U.S. Cl.
CPC . *G01N 33/54366* (2013.01); *G01N 2333/726* (2013.01)

(58) Field of Classification Search
CPC .............. G01N 33/54366; G01N 2333/726
See application file for complete search history.

(56) References Cited

U.S. PATENT DOCUMENTS

| 7,155,959 B2 | 1/2007 | Su et al. |
| 7,179,784 B2 | 2/2007 | Zhang et al. |

(Continued)

OTHER PUBLICATIONS

Vidic et al., Quantitative assessment of olfactory receptors activity in immobilized nanosomes: a novel concept for bioelectronic nose, May 2006, Lab Chip, 6: pp. 1026-1032.*

(Continued)

*Primary Examiner* — Mark Shibuya
*Assistant Examiner* — Gary E Hollinden
(74) *Attorney, Agent, or Firm* — Carolyn S. Elmore; Mahreen Chaudhry Hoda; Elmore Patent Law Group, P.C.

(57) ABSTRACT

The invention provides a bio-sensing nanodevice comprising: a stabilized biologically-derived G-protein coupled receptor—the olfactory receptor—on a support, a real time receptor-ligand binding detection method, an odorant delivery system and an odorant recognition program. The biologically-derived G-protein coupled receptor can be stabilized on nanotechnology using surfactant peptide. The said nanodevice provides a greater surface area for better precision and sensitivity to odorant detection. The invention further provides a microfluidic chip containing a stabilized biologically-derived G-protein coupled receptor—the olfactory receptor—immobilized on a support, and arranged in at least two dimensional microarray system. The invention also provides a method of delivering odorant comprising the step of manipulating the bubbles in complex microfluidic networks wherein the bubbles travel in a microfluidic channel carrying a variety of gas samples to a precise location on a chip. The invention further provides method of fabricating hOR17-4 olfactory receptor.

2 Claims, 13 Drawing Sheets

(56) References Cited

U.S. PATENT DOCUMENTS

| | | | |
|---|---|---|---|
| 8,748,111 B2* | 6/2014 | Mershin | G01N 21/553 422/83 |
| 2002/0019015 A1* | 2/2002 | Lahiri et al. | 435/7.9 |
| 2002/0076755 A1* | 6/2002 | Kuliopulos et al. | 435/69.1 |
| 2003/0008344 A1 | 1/2003 | Adler et al. | |
| 2003/0030817 A1* | 2/2003 | Lee et al. | 356/491 |
| 2003/0176335 A1 | 9/2003 | Zhang et al. | |
| 2005/0130197 A1 | 6/2005 | Do et al. | |
| 2005/0176009 A1 | 8/2005 | Lancet et al. | |
| 2006/0172279 A1 | 8/2006 | Smela et al. | |
| 2006/0280430 A1 | 12/2006 | Rabinow et al. | |
| 2007/0006926 A1 | 1/2007 | Prakash et al. | |
| 2007/0116607 A1 | 5/2007 | Wang et al. | |

OTHER PUBLICATIONS

Yeh et al., Peptergents: peptide detergents that improve stability and functionality of a membrane protein, glycerol-3-phosphate dehydrogenase, 2005, Biochem, 44: pp. 16912-16919.*

Zhao et al., Designer short peptide surfactants stabilize G protein-coupled receptor bovine rhodopsin, Nov. 2006, PNAS, 103(47): pp. 17707-17712.*

Hatt, Molecular and cellular basis of human olfaction, 2004, Chemistry & Biodiversity, 1: pp. 1857-1869.*

Vidic, J.M., et al., "Quantitative assessment of olfactory receptors activity in immobilized nanosomes: a novel concept for bioelectronic nose," Lab Chip, 6:1026-1032 (2006).

Maguire, Y, et al., "Ultra-small-sample molecular structure detection using microsolt waveguide nuclear spin resonance," PNAS, 104(22):9198-9203 (2007).

Xu, Fen et al., "Simple approach to highly oriented ZnO nanowire arrays: large-scale growth, photoluminescence and photocatalytic properties," Nanotechnology, 17:588-594 (2006).

U.S. Appl. No. 13/015,851, filed Jan. 28, 2011, Mershin et al.

* cited by examiner

US 9,714,941 B2

BIO-SENSING NANODEVICE

RELATED APPLICATIONS

This application claims the benefit of U.S. Provisional Application No. 60/953,030, filed on Jul. 31, 2007. The entire teaching of the above application is incorporated herein by reference.

GOVERNMENT SUPPORT

This invention was made with government support under Grant No. CCF0122419 awarded by the National Science Foundation. The government has certain rights in this invention.

BACKGROUND OF THE INVENTION

The emerging field of bioelectronics seeks to exploit biology in conjunction with electronics in a wider context encompassing, for example, micro or nanoscale biomaterials for information processing, information storage and actuators. A key aspect is the interface between biological materials and electronics since it defines the target, sensitivity, selectivity and speed of the device.

The detection of odorants has also been pursued through the development of electronic noses that are used for environmental monitoring, medical testing, and food and drink production. In the most sophisticated systems, a unique chemical fingerprint can be generated by an array of sensors and then identified by pattern-recognition techniques, such as the smell of a rose (Lundstrom, I., *Nature*, 406:682-3, 2000). Attempts to measure odors with electronic instruments were made in the 1950s, but the modern field of artificial olfaction, according to Lundstrom (Lundstrom, I., *Nature*, 406:682-3, 2000), began in 1982 with the work of Persaud and Dodd (Persaud, K., and Dodd G., *Nature*. 299:352-5, 1982). They used a small array of gas-sensitive metal-oxide devices to classify odors. While there has been a steady increase in the number of systems using chemical sensor arrays, their success depends not only on the development of new sensor technologies, but also on the availability of powerful pattern-recognition software (Lundstrom, I., *Nature*, 406:682-3, 2000). This last aspect is particularly important for sensor arrays that produce a composite response for detecting targets that emit a characteristic array of odorants. However, these systems suffer from many limitations that are superseded by the olfactory cells in animals.

Olfactory receptor neurons (olfactory cells) are bipolar nerve cells that densely line the olfactory membrane in the recess of the nose, wherein odor receptor proteins that respond to odor molecules, called olfactory receptors, are expressed at high density. In olfactory cells, the chemical substances diffusing in the air from the stimulus source are detected by olfactory receptors and converted to neural signals. These neural signals are transmitted to the brain through the olfactory bulb (mitral cells or tufted cells) and the olfactory cortex such as the piriform cortex (pyramidal cells) and allow humans to sense odors. The interaction of odorants with olfactory receptors on the apical cilia of olfactory neurons is the first step in the perception of smell. The large number (e.g., approximately ~350 in human and ~1200 in dog) and structural diversity of the opsin-like GPCRs that function as olfactory receptors underlies the ability to detect and discriminate a vast number of volatile compounds (Buck, L. and Axel, R., *Cell* 65: 175-187, 1991; Fuchs, T. et al., *Hum. Genet.* 108: 1-13, 2001). Olfactory receptors interact with a diverse array of volatile molecules. It is widely accepted that every odorous molecule binds to several ORs0 and vise versa. This binding pattern generates a unique combinatorial code that generates a specific aroma for each odorant and enables the organism to distinguish it from other molecules. This system is highly sensitive and allows to discriminate between two protein isomers and at times even between two optical enantiomers.

Not withstanding recent advances in bioelectronic sensing device, a quest for real time bio-sensing nanodevices with improved speed, precision and sensitivity still remains.

SUMMARY OF THE INVENTION

The invention provides a bio-sensing nanodevice comprising: a stabilized biologically-derived G-protein coupled receptor—the olfactory receptor—on a support embedded in a microfluidic device, a real time receptor-ligand binding detection method, an odorant delivery system and an odorant recognition program. The biologically-derived G-protein coupled receptor can be stabilized on nanotechnology using surfactant peptides. The said nanodevice provides a greater surface area for better precision and sensitivity to odorant detection. The invention further provides a microfluidic chip containing a stabilized biologically-derived G-protein coupled receptor immobilized on a support, and arranged in at least two dimensional microarray system. The invention also provides a method of delivering odorant comprising the step of manipulating the bubbles in complex microfluidic networks wherein the bubbles travel in a microfluidic channel carrying a variety of gas samples to a precise location on a chip. The invention further provides method of fabricating hOR17-4 olfactory receptor.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
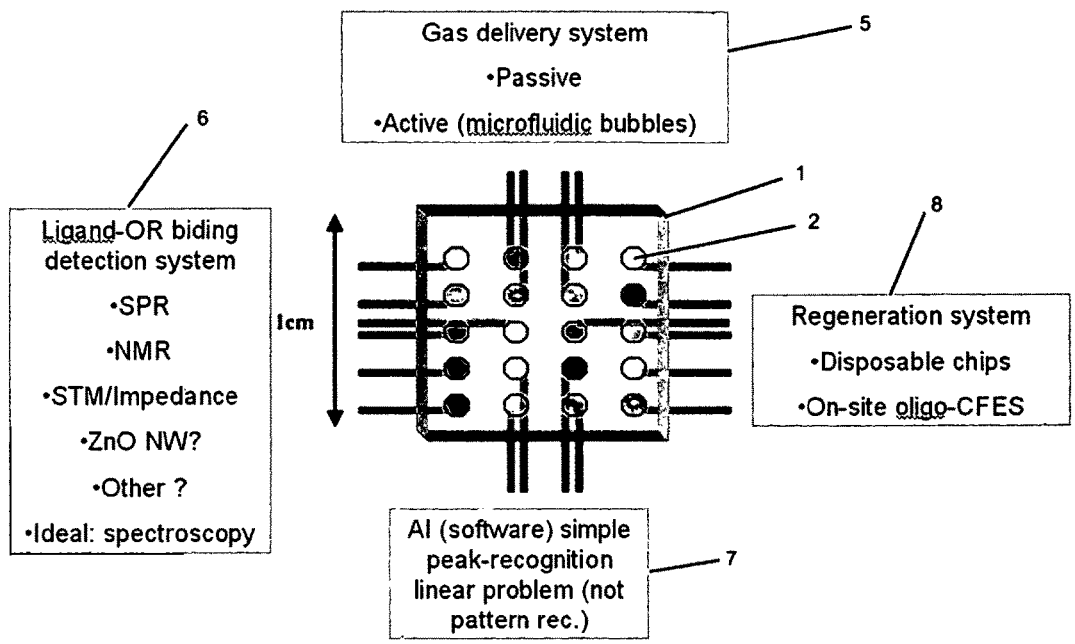
FIG. 1 illustrates elements of an exemplary bio-sensing nanodevice according to the invention.

The present invention features a bio-sensing nanodevice comprising: a stabilized biologically-derived G-protein coupled receptor [2]—the olfactory receptor—on a support, a real time receptor-ligand binding detection method [6], an odorant delivery system [5] and an odorant recognition program [7]. The biologically-derived G-protein coupled receptor [2] can be stabilized on nanotechnology using surfactant peptide. The said nanodevice provides a greater surface area for better precision and sensitivity to odorant detection.

In one embodiment, the G-protein coupled receptor [2] is stabilized with a surfactant peptide. G-protein coupled receptors are cell-membrane 7-transmembrane-type receptors coupled with trimeric G-protein. This type further falls into the cAMP system producing cAMP as the second messenger and the inositol phospholipid transmitter system producing inositol-1,4,5-triphosphate ($IP_3$) or diacyl glycerol (DG) as the second messenger. cAMP can activate some pathways in single or parallel. In some types of nerve cells, such as olfactory-receptor nerve cells, cAMP-dependent ion-channels are opened, the cellular membrane is depolarized, and $Ca^{2+}$ enters the cell through the channel, transiently increasing intracellular $Ca^{2+}$ concentration. cAMP activates cAMP-dependent kinase (A kinase), phosphorylates serine and/or threonine residues of function-protein, and modifies its activity. On the other hand, $IP_3$ binds to $IP_3$ receptors on the endoplasmic reticulum and accelerates the release of $Ca^{2+}$ into a cell. Diacyl glycerol promotes the action of hormones and the like by activating C kinase.

In one preferred embodiment, the G-protein coupled receptor [2] is an olfactory receptor, preferably hOR17-4. The olfactory receptor is preferably stabilized. Stabilization can be accomplished by mixing the olfactory receptor with a surfactant. A preferred class of surfactants is protein stabilizing surfactants, such as surfactant peptides. The surfactants of the present invention preferably self-assemble in solution. The surfactant, together with the olfactory system, forms a new self-assembled nanostructure. The surfactants are amphiphilic molecules that tend to aggregate in order to isolate the hydrocarbon chain from contact with water. The common feature for this self-association is the formation of a polar interface, which separates the hydrocarbon and water regions, in many instances, forming a spherical micelle consisting of typically 50-100 lipid molecules arranged so that their hydrocarbon tails form the interior of the micelle, and the polar head groups act as a shield against the surrounding water. Depending on the surfactant and its concentration, various structures can be found, including liposomes, lamellar phase, and hexagonal, cubic or tubular structures.

The surfactant peptides used in accordance with the present invention will be preferably peptides having a formula selected from the group consisting of:

| Sequence (N → C) | Formula |
| --- | --- |
| $(\Phi)_m(+)_n$ | 1 |
| $(+)_n(\Phi)_m$ | 2 |
| $(\Phi)_m(-)_n$ | 3 |
| $(-)_n(\Phi)_m$ | 4 |
| $(-)_n(\Phi)_m(-)_n$ | 5 |
| $(+)_n(\Phi)_m(+)_n$ | 6 |
| $(\Phi)_m(-)n(\Phi)_m$ | 7 |
| $(\Phi)_m(+)n(\Phi)_m$ | 8 |
| $(+)_n(\Phi)_m(-)_n$ | 9 |
| $(-)_n(\Phi)_m(+)_n$ | 10 | wherein:

($\Phi$) represents independently for each occurrence, a natural or non-natural amino acid comprising a hydrophobic sidechain; preferably alanine, valine, leucine, isoleucine or proline;

(+) represents independently for each occurrence a natural or non-natural amino acid comprising a sidechain that is cationic at physiological pH; preferably histidine, lysine or arginine;

(−) represents independently for each occurrence a natural or non-natural amino acid comprising a sidechain that is anionic at physiological pH; preferably aspartic acid or glutamic acid;

wherein the terminal amino acids are optionally substituted;

m for each occurrence represents an integer greater than or equal to 5; and n for each occurrence represents an integer greater than or equal to 1;

under conditions suitable for self-assembly of the peptides into a nanostructure and allowing the nanostructure to be formed.

In one aspect the peptides having the formula 1, 3, 4, 5, 7, 8, or 10 and the N terminal amino acid can be substituted by an acyl (e.g. acetyl or butyloxycarbonyl group) or other blocking group to remove the terminal charge and the peptides have the formula 1, 2, 4, 6, 7, 8, or 10 and the C terminal amino acid can be substituted by an amino or alcohol group to form an amide or ester, or other blocking group to remove the terminal charge. Indeed, one or both termini and any side chains residues can be optionally blocked or further substituted to modify (remove or add) charge, and/or increase or decrease hydrophobicity and/or hydrophilicity of the surfactant. Blocking groups that can be used to control charge, hydrophobicity or the ability to self-assemble in the surfactant include esters and amides of carboxylic acids, silyl ethers of alcohols, and acetals and ketals of aldehydes and ketones, respectively. The field of protecting group chemistry has been reviewed (Greene, T.

W.; Wuts, P. G. M. Protective Groups in Organic Synthesis, 2nd ed.; Wiley: N.Y., 1991), which is incorporated by reference.

Most preferably, the surfactant peptide is selected from:

| | |
|---|---|
| AAAAAAD, | (SEQ ID NO. 1) |
| VVVVVVD, | (SEQ ID NO. 2) |
| AAAAAADD, | (SEQ ID NO. 3) |
| VVVVVVDD, | (SEQ ID NO. 4) |
| LLLLLLDD, | (SEQ ID NO. 5) |
| KKIIIIII, | (SEQ ID NO. 6) |
| KKLLLLLL, | (SEQ ID NO. 7) |
| KKAAAAAA, | (SEQ ID NO. 8) |
| KKVVVVVV, | (SEQ ID NO. 9) |
| DDDDDDDDDDAAAAAAAAAA, | (SEQ ID NO. 10) |
| AAAAAAAAAADDDDDDDDDD, | (SEQ ID NO. 11) |
| EEEEEEEEEEAAAAAAAAAA, | (SEQ ID NO. 12) |
| AAAAAAAAAAEEEEEEEEEE, | (SEQ ID NO. 13) |
| DDDDDDDDDDVVVVVVVVVV, | (SEQ ID NO. 14) |
| VVVVVVVVVVDDDDDDDDDD, | (SEQ ID NO. 15) |
| DDDDDDDDDDPPPPPPPPPP, | (SEQ ID NO. 16) |
| PPPPPPPPPPDDDDDDDDDD, | (SEQ ID NO. 17) |
| AAAAAAAAAAHHHHHHHHHH, | (SEQ ID NO. 18) |
| HHHHHHHHHHAAAAAAAAAA, | (SEQ ID NO. 19) |
| KKKKKKKKKKAAAAAAAAAA, | (SEQ ID NO. 20) |
| AAAAAAAAAAKKKKKKKKKK, | (SEQ ID NO. 21) |
| RRRRRRRRRRAAAAAAAAAA, | (SEQ ID NO. 22) |
| AAAAAAAAAARRRRRRRRRR, | (SEQ ID NO. 23) |
| DDDDDDDDDDAAAAAAAAAADDDDDDDDDD, | (SEQ ID NO. 24) |
| EEEEEEEEEEAAAAAAAAAAEEEEEEEEEE, | (SEQ ID NO. 25) |
| DDDDDDDDDDVVVVVVVVVVDDDDDDDDDD, | (SEQ ID NO. 26) |
| DDDDDDDDDDPPPPPPPPPPDDDDDDDDDD, | (SEQ ID NO. 27) |
| HHHHHHHHHHAAAAAAAAAAHHHHHHHHHH, | (SEQ ID NO. 28) |
| KKKKKKKKKKAAAAAAAAAAKKKKKKKKKK, | (SEQ ID NO. 29) |
| RRRRRRRRRRAAAAAAAAAARRRRRRRRRR, | (SEQ ID NO. 30) |
| AAAAAAAAAADDDDDDDDDDAAAAAAAAAA, | (SEQ ID NO. 31) |
| AAAAAAAAAAEEEEEEEEEEAAAAAAAAAA, | (SEQ ID NO. 32) |
| VVVVVVVVVVDDDDDDDDDDVVVVVVVVVV, | (SEQ ID NO. 33) |
| PPPPPPPPPPDDDDDDDDDDPPPPPPPPPP, | (SEQ ID NO. 34) |
| AAAAAAAAAAHHHHHHHHHHAAAAAAAAAA, | (SEQ ID NO. 35) |
| AAAAAAAAAAKKKKKKKKKKAAAAAAAAAA, | (SEQ ID NO. 36) |
| AAAAAAAAAARRRRRRRRRRAAAAAAAAAA, | (SEQ ID NO. 37) |
| KKKKKKKKKKAAAAAAAAAADDDDDDDDDD, | (SEQ ID NO. 38) |
| KKKKKKKKKKAAAAAAAAAAEEEEEEEEEE, | (SEQ ID NO. 39) |
| RRRRRRRRRRVVVVVVVVVVDDDDDDDDDD, | (SEQ ID NO. 40) |
| KKKKKKKKKKPPPPPPPPPPDDDDDDDDDD, | (SEQ ID NO. 41) | and

| | |
|---|---|
| HHHHHHHHHHAAAAAAAAAAEEEEEEEEEE. | (SEQ ID NO. 42) |

Each of the above amino acid designations, (e.g., A, D, E, etc.) are intended to include substituted or blocked forms, e.g. N-acetyls or COO-alkyls. Further discussion on the surfactant oligopeptides and di- and tri-block peptide copolymers can be found in U.S. Pat. No. 7,179,784, and is hereby incorporated by reference.

In one instance of the invention, biologically-derived G-protein coupled receptor [2] is immobilized on a support [15]. Examples of materials used for supports include any material capable of forming a solid surface, such as, without limitation, gold, silver, platinum, glass, silica, silicon, ceramics, silicon dioxide, plastics, metals (including alloys), naturally-occurring and synthetic polymers (e.g., polystyrene, cellulose, chitosan, dextran, and nylon), and the like. A support [15] may be formed of layers made of a plurality of materials. For example, a support may be made of an inorganic insulating material, such as glass, quartz glass, alumina, sapphire, forsterite, silicon oxide, silicon carbide, silicon nitride, or the like. A support [15] may be made of an organic material, such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene-acrylonitrile co-polymer, acrylonitrile-butadiene-styrene co-polymer, silicone resin, polyphenylene oxide, polysulfone, and the like. Also in the present invention, nitrocellulose film, nylon film, PVDF membrane, or the like, which are used in blotting, may be used as a material for a support [15]. When a material constituting a support is in the solid phase, such as a support is herein particularly referred to as a "solid phase support". A solid phase support [15] may herein take the form of a plate, a microwell plate, a chip, a glass slide, a film, beads, a metal (surface), or the like. A support may or may not be coated.

The term "coating" in relation to a solid phase support or substrate refers to an act of forming a film of a material on a surface of the solid phase support or substrate, and also refers to a film itself. Coating is performed for various purposes, such as, for example, improving the quality of a solid phase support and substrate (e.g., elongation of life span, improvement in resistance to hostile environment, such as resistance to acids, etc.), affinity to a substance integrated with a solid phase support or substrate, and the like. Various materials may be used for such coating, including, without limitation, biological substances (e.g., DNA, RNA, protein, lipid, etc.), polymers (e.g., poly-L-lysine, MAS (available from Matsunami Glass, Kishiwada, Japan), and hydrophobic fluorine resin), silane (APS (e.g., γ-aminopropyl silane, etc.)), metals (e.g., gold, etc.), in addition to the above-described solid phase support and substrate. The selection of such materials is within the technical scope of those skilled in the art and thus can be performed using techniques well known in the art.

Immobilization of the biologically-derived G-protein coupled receptor [2] onto the support [15] can be achieved by various methods known in the art. One example uses the self biologically-derived G-protein coupled receptor [2] must be attached to the metal oxide nanowires. The biologically-derived G-protein coupled receptor [2] can be bound to the nanowire covalently or non-covalently through the biologically-derived G-protein coupled receptor [2] or through the surfactant or other organic/inorganic intermediates (adapters). Direct attachment (where biologically-derived G-protein coupled receptor [2] directly contacts the metal oxide nanowire surface) and indirect attachment (where intermediate layers are required for attachment) are included. In the context of this invention, methods of attachment of biologically-derived G-protein coupled receptors [2] (such as olfactory receptors) to the metal oxide nanowires include, but are not limited to, covalent chemical coupling, photochemical cross-linking, surface coating/modification, gold surface chemistry, protein affinity tags, biotin-streptavidin linkages, antibody immobilization, and engineered surface-binding peptide sequences.

Another method is the direct attachment of the biologically-derived G-protein coupled receptor [2] on metal oxides using peptide binding sequences. For example, in the case of ZnO nanowires, the biologically-derived G-protein coupled receptor can be directly attached to ZnO nanowires using a ZnO-binding peptide sequence. These binding peptide sequences are obtained by screening a vast combinatorial library of random peptide sequences for binding to the metal oxide surface. To allow binding sequences to be enriched, the peptides are coupled to a biological vector. Some examples are viruses (phage display), cell surface display (using bacteria or yeast), or small biomolecules (ribosomes or antibodies). For a review of these methods, please see Sarikaya et al. (2003) "Molecular biomimetics: nanotechnology through biology" *Nature Materials.* 2(9), 577-585. A typical protocol consists of incubating the peptide library (attached to a biological vector) with the metal oxide surface, then washing the surface thoroughly to remove sequences that bind weakly. Those that bind strongly are then eluted from the surface with a low pH buffer and the population amplified by allowing the vector to multiply. These screened binding sequences can be determined by direct sequencing. The process is repeated with increasingly stringent wash conditions until only one or several binding peptide sequences remain, which will bind the surface with high affinity.

A specific example for such a method is the use of an M13 bacteriophage library (phage display) to generate ZnO nanowire-binding sequences. This protocol has been adapted from Whaley et al. (2000) "Selection of peptides with semiconductor binding specificity for directed nanocrystal assembly" *Nature.* 405, 665-668. The library contains approximately 1 billion ($10^9$) random peptide sequences expressed on the viral coat which are screened for their ability to bind ZnO nanowires. After washing, the bound phage are eluted (pH 2.2) and amplified by allowing them to infect their bacterial host (*E. Coli* ER2537). After 5-6 successively more stringent rounds of selection an optimal ZnO-binding sequence is determined.

Examples of a ZnO-binding sequence includes, but not limited to, RSNTRMTARQHRSANHKSTQRARS (SEQ ID NO. 43) or a binding fragment thereof, GLHIPTSHR (SEQ ID NO. 44), EAHVMHKVAPRP (SEQ ID NO. 45), and RIGHGRQIRKPL (SEQ ID NO. 46). The coupling can be accomplished synthetically or recombinantly (Thai C K, et al., *Biotechnol. Bioeng.,* 2004, 87, 129-137, which is hereby incorporated by reference by its entirety). The ZnO-binding peptide sequence direct method offers the advantage of controlling directionality of the PSI protein so that electron ejection is directed to the electrode surface, limiting the distance between the PSI protein and semiconductor and simplifies the procedure by eliminating semiconductor pretreatment.

As used herein the term "nanowire" means a wire (or other filamentous structure) with a diameter scale on the order of nanometers (nm). Growth of nanowires having various aspect ratios, including nanowires with controlled diameters, is described in, e.g., Gudiksen et al. (2000) "Diameter-selective synthesis of semiconductor nanowires" *J. Am. Chem. Soc.* 122, 8801-8802; Cui et al. (2001) "Diameter-controlled synthesis of single-crystal silicon nanowires" *Appl. Phys. Lett.* 78, 2214-2216; Gudiksen et al. (2001) "Synthetic control of the diameter and length of single crystal semiconductor nanowires" *J. Phys. Chem. B* 105, 4062-4064; Morales et al. (1998) "A laser ablation method for the synthesis of crystalline semiconductor nanowires" *Science* 279, 208-211; Duan et al. (2000) "General synthesis of compound semiconductor nanowires" *Adv. Mater.* 12, 298-302; Cui et al. (2000) "Doping and electrical transport in silicon nanowires" *J. Phys. Chem. B* 104, 5213-5216; Peng et al. (2000) "Shape control of CdSe nanocrystals" *Nature* 404, 59-61; Puntes et al. (2001) "Colloidal nanocrystal shape and size control: The case of cobalt" *Science* 291, 2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 6,036,774 to Lieber et al. (Mar. 14, 2000) entitled "Method of producing metal oxide nanorods"; U.S. Pat. No. 5,897,945 to Lieber et al. (Apr. 27, 1999) entitled "Metal oxide nanorods"; U.S. Pat. No. 5,997,832 to Lieber et al. (Dec. 7, 1999) "Preparation of carbide nanorods"; Urbau et al. (2002) "Synthesis of single-crystalline perovskite nanowires composed of barium titanate and strontium titanate" *J. Am. Chem. Soc.,* 124, 1186; and Yun et al. (2002) "Ferroelectric Properties of Individual Barium Titanate Nanowires Investigated by Scanned Probe Microscopy" *Nanoletters* 2, 447. The nanowires of this invention can be substantially homogeneous in material properties, or in certain embodiments can be heterogeneous (e.g., nanowire heterostructures). The nanowires can be fabricated from essentially any convenient material or materials, and can be, e.g., substantially crystalline, substantially monocrystalline, polycrystalline, or amorphous. It should be appreciated that although nanowires are frequently referred to, nanostructures, such as nanorods, nanotubes, nanotetrapods, nanoribbons and/or combinations thereof can also be employed.

The metal oxide nanowires used accordance with this invention include, but are not limited to, titanium oxide, zinc oxide, tin oxide, alumina, zirconia, ceria, silica, yttria, boronia, magnesia, strontium titanate, potassium titanate, barium titanate, calcium titanate, calcia, ferrite, hafnia, tungsten trioxide, iron oxide, copper oxide, nickel oxide, cobalt oxide, barium oxide, strontium oxide, vanadium oxide, indium oxide, barium titanate, aluminosilicate, niobium oxide and calcium phosphate. These compounds can be selected depending on the intended use, and may be used singly or in combination. Among these metal oxide nanowires, titanium oxide, zinc oxide, tin oxide, indium oxide and tungsten oxide are most preferable due to the wide energy gaps of 3 eV or wider.

For example, to form GaAs semiconductor nanocrystals, a solution of Ga and As precursors may be prepared by dissolving an organic complex of Ga and As powder into tributyl phosphine. About 2 ml of this solution (kept at −10° C.) may then be quickly injected into about 4 grams of a heated bath comprising a binary mixture of (99% pure) tri-octyl phosphine oxide (TOPO) and 17 molar % hexyl phosphonic acid (HPA) which had been preheated to a temperature of about 360° C. After the injection, the temperature of the binary mixture bath drops to approximately 300° C. and is kept at this temperature for about 5-10 minutes for the fast growth of rod-like GaAs semiconductor nanocrystals. After this time period, the binary mixture bath is rapidly cooled. The same procedure may be used to form spherical semiconductor nanocrystals by reducing the concentration of the HPA down to, for example, about 4 molar % and increasing the reaction time at 300° C. up to several hours. Similar results may be obtained substituting other particular Group III metals (Al or In) for Ga and/or substituting other particular Group v precursors (P or Sb) for As.

To form CdSe semiconductor nanocrystals, a solution of Cd and Se precursors is prepared by dissolving 0.82 grams of $Cd(CH_3)_2$ and 0.4 grams of Se powder into 15.3 grams of tributyl phosphine. 2 ml of this solution (kept at −10° C.) was then quickly injected into 4 grams of a heated bath comprising a binary mixture of (99% pure) tri-octyl phosphine oxide (TOPO) and 17 molar % hexyl phosphonic acid (HPA) which had been preheated to a temperature of about 360° C. After the injection, the temperature of the binary mixture bath drops to approximately 300° C. and is kept at this temperature for about 5-10 minutes for the fast growth of rod-like semiconductor nanocrystals. After this time period, the binary mixture bath is rapidly cooled. The same procedure may be used to form spherical semiconductor nanocrystals by reducing the concentration of the HPA down to, for example, about 4 molar % and increasing the reaction time at 300° C. up to several hours.

To form ZnO nanowires, ZnO powder and graphite powder can be mixed in a weight ratio 1:3 to 3:1 and loaded into a graphite boat, placed into a quartz tube being flushed with Ar gas with a flow rate between 100 and 2000 sccm. The gas can contain between 1 and 10 ppm oxygen. A (100) $SrTiO_3$ single crystal substrate coated with a film of gold with a thickness between 1 and 100 nm can be placed in the tube downstream of the graphite boat where the temperature gradient between the graphite boat and the substrate can be approximately 300° C. The quartz tube can be heated to between 900° C. and 1000° C. for 0.25 to 1 hour to grow the nanowires. Alternatively, zinc metal can be used as the metal vapor source, in which case the tube furnace was heated to between 500° C. and 700° C. The nanowires can be grown on the single crystal surface in a uniform diameter and length, ranging from 10 to 50 nm and 1 to 2 μm, respectively.

In a preferred embodiment, the nanowires can be grown from a ZnO foil. One such protocol that has been used in obtaining functional bio-photovoltaic devices was as follows: A 0.075 M $ZnSO_4$ aqueous solution (40 ml) containing $NH_4Cl$ (molar ratio of $NH^{+4}/Zn^{+2}=20:1$) was formed. The pH was adjusted to 11.7 with NaOH pellets. Pieces of 0.25 $cm^2$ Zn foil were suspended in the solution and the vial containing the solution was transferred to a water bath at 60° C. and left overnight for 12-15 h at 60° C. The effects of varying pH were studied showing that at pH 13, the nanowires produced were black in color indicating a lower bandgap. This process requires very little heat and only a small number of steps and does not require the use of harmful chemicals. The varying of the pH levels provides an improvement over the protocol of F. Xu et al. (*Nanotechnology* 17 (2006) 588-594), which is hereby incorporated by reference by its entirety.

In one embodiment, the real time receptor-ligand binding detection method [6] of the bio-sensing nanodevice is selected from Surface Plasmon Resonance (SPR), micro-slot nuclear magnetic resonance (microNMR), scanning tunneling microscopy (STM)/impedance spectroscopy, atomic force microscopy (AFM), ZnO nanowire surface passivation, optical microscopes, confocal microscopes, and reading devices using a laser light source. In a preferred embodiment, the receptor-binding detection method is selected from ultraviolet-visible absorption and fluorescence resonant energy transfer. The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jonsson et al. (1993) Ann. Biol. Clin. 51:19; Jonsson et al. (1991) Biotechniques 11:620-627; Johnsson et al. (1995) J. Mol. Recognit. 8:125; and Johnnson et al. (1991) Anal. Biochem. 198:268.

The term surface passivation is used to refer to the formation of a protective oxide (preferably ZnO) or nitride layer on the surface of the metallic layer freshly deposited by the process of the invention. Such passivation is produced, without limitation, by a plasma source or ion beam operated in the presence of molecular oxygen and/or nitrogen to produce an activated layer of molecular, ionized and atomic particles that passivate the surface of the metal layer being treated, particularly aluminum, by the formation of superficial oxides and/or nitrides.

Optical sensors for fluorescence or luminescence have the ability to detect emitted light of very low intensity at specific wavelengths and the ability to block light at other wavelengths which can interfere with the signal being detected. Such sensors are often used in conjunction with the application of molecules known as fluorescent probes. Many fluorescent probes have been designed to localize components within a biological specimen or to respond to a specific stimulus. Because of the maturity of fluorescent probe technology, probes can be obtained from many manufacturers, including Invitrogen (Carlsbad, Calif.), Martek Biosciences Corporation (Columbia, Md.), and Sigma-Aldrich Corporation (St. Louis, Mo.). Specific useful probes can indicate a broad set of cellular features and properties such as ion concentration, proteins, nucleic acids, pH, membrane potential, and other characteristics known to those skilled in the art.

Fluorescence sensing systems typically have at least four components: (1) a light source; (2) optical filters; (3) detectors (i.e., light sensors); and (4) signal processing circuitry. The light source is designed to deliver sufficient optical power, the filters to be capable of discriminating wavelengths, and the detectors to distinguish fluorescent emission, even in the presence of interfering excitation light. The cell must be illuminated within an appropriate range of wavelengths in order for the fluorescence to occur. This "excitation" light can be generated by a separate component integrated with the system such as a vertical-cavity surface-emitting laser (VCSEL) or a light emitting diode (LED) or by a semiconductor photon source integrated on-chip. The light can be directly shone on the cells or guided to the cells using an optical waveguide integrated on-chip.

Optical sensors for imaging the cells have the ability to measure light intensity using a dense array of photosensitive pixels. For the purposes of this invention, such sensors can be used in either a conventional imaging configuration with optical elements such as lenses that focus the image onto an imaging array as in a standard camera or light microscope, or in a "contact" imaging configuration which does not use intervening optics and which generates a representation of a specimen directly coupled to the surface of the chip. The photosensitive elements of the contact imager capture light that is transmitted through the cells. Preferably, imagers are compatible with CMOS technology to enable the implementation of other sensors and circuitry on the same substrate. Many pixel designs are suitable for imagers and are well known in the field of digital imaging technology, including passive pixels, current-mode pixels, and active pixel sensor (APS) pixels.

As used herein, the term "real time" means that a certain state is substantially simultaneously displayed in another form (e.g., as an image on a display or a graph with processed data). In such a case, the "real time" lags behind an actual event by the time required for data processing. Such a time lag is included in the scope of "real time" if it is substantially negligible. Such a time lag may be typically within 10 seconds, and preferably within 1 second, without limitation. A time lag exceeding 10 seconds may be included in the scope of "real time" for certain uses.

In one embodiment, the odorant delivery system [5] of the bio-sensing nanodevice can be either passive exposure to air or microfluidic bubble logic operation. The microfluidic bubble logic operation comprises micron-sized droplets and bubbles of chemical in a microfluidic chip. Control of routing of packets of gas bubbles in a microfluidic chip allows for implementation of complex detection schemes. The term "bubble logic" employs micron-sized (nanoliters) droplets and bubbles of chemicals to mimic the actions of the electrons moving through the circuits of a microprocessor. Thus bubbles traveling in a microfluidic channel can carry a variety of gas samples to precise locations on a chip. They can be stored in memory elements, routed on-chip, merged or split and transported at high throughputs. The term "microfluidic" generally refers to a system or device having channels and chambers that are fabricated with a cross-sectional dimension (e.g. depth, width, or diameter) of less than a millimeter. The channels and chambers typically form fluid channel networks that allow the transportation, mixing, separation and detection of very small quantities of materials. Microfluidics are particularly advantageous because they make it possible to perform various chemical and biochemical reactions, macromolecular separations, and the like with small sample sizes, in automatable, high-throughput processes. Microfluidic systems are particularly well adapted for analyzing small sample sizes. Sample sizes are typically are on the order of nanoliters and even picoliters. Similar apparatus and methods of fabricating microfluidic devices are also taught and disclosed in U.S. Pat. Nos. 5,858,195; 5,126,022; 4,891,120; 4,908,112; 5,750,015; 5,580,523; 5,571,410; 5,885,470; and 6,793,753 incorporated herein by reference.

Microfluidic devices can be fabricated out of any material that has the necessary characteristics of chemical compatibility and mechanical strength. One exemplary material is silicon since a wide range of advanced microfabrication and micromachining techniques have been developed for it and are well known in the art. Additionally, microfluidic devices can be produced directly in electrically insulating materials. The most widely used processes include isotropic wet chemical etching of glass or silica and molding of plastics. The channels are typically defined by photolithographic techniques and etching away the material from around the channel walls produces a freestanding thin walled channel structure. Freestanding structures can be made to have very thin or very thick walls in relation to the channel width and height. The walls, as well as the top and bottom of a channel can all be of different thickness and can be made of the same material or of different materials or a combination of materials such as a combination of glass, silicon, and a biologically-compatible material such as PDMS. Sealed channels or chambers can be made entirely from biologically-compatible material such as PDMS.

In one embodiment, the odorant recognition program [7] of the bio-sensing nanodevice comprises a 1 dimensional peak-recognition program. For instance, the system is first "trained" on known odorants and the signatures are recorded. Then the system is exposed to unknown odorants or combinations of odorants and the signatures are matched with the known database of odors. Thus, the products and methods of the inventions can be used in a number of commercially interesting areas. For example, the devices can detect the presence, absence or quality of specific odoriferous chemical compounds or biological substances (including bacteria, mold, mildew, fungi, and viruses). It can be used to detect the presence of illegal substances or controlled substances (e.g., in an airport, customs or similarly controlled environment), It can be used to detect pathogens or toxins, such as in an air quality management program in a residential, industrial or other working or living environment. It can be used to detect contaminants in products, such as food, drugs, medical devices, sterile products, and the like. It can be used to determine the quality or acceptability of food products, drugs, consumer products and perfumes. It can be used in medical fields and diagnostics by detecting human odors, including the breath or other body odors. It can be used to detect, identify or locate materials, including chemicals, tissues and the like, such as in industrial, medical and forensics applications. In another embodiment, application software for measurement and presentation typically includes software for setting conditions for applying stimuli or conditions for recording detected signals. With such a measurement and presentation application, a computer can have a means for applying a stimulus to cells and a means for processing signals detected from cells, and in addition, can control an optically observing means (a SIT camera and an image filing device) and/or a cell culturing means. As such, the invention can include a computer processing unit which is programmed to identify a test composition's "fingerprint" (e.g., the specific combination of receptors that are activated and/or not activated) and compare it to one or more standards (e.g., the specific combination of receptors that are activated and/or not activated) and identify the exact match or close match(es).

Real time display can also be performed using techniques well known in the art. For example, after all images are obtained and stored in a semi-permanent memory, or substantially at the same time as when an image is obtained, the image can be processed with appropriate application software to obtain processed data. For example, data may be processed by a method for playing back a sequence of images without interruption, a method for displaying images in real time, or a method for displaying images as a "movie" or "streaming" showing irradiating light as changes or continuation on a focal plane. By inputting stimulus variables on a parameter setting screen using a keyboard, a touch panel, a mouse, or the like, it is possible to set desired complicated conditions for stimulation. In addition, various conditions, such as a temperature for cell culture, pH, and the like, can be set using a keyboard, a mouse, or the like. A display screen displays a time-lapse profile detected from a cell or information derived therefrom in real time or after recording. In addition, another recorded profile or information derived from of a cell can be displayed while being superimposed with a microscopic image of the cell. In addition to recorded information, measurement parameters in recording (stimulation conditions, recording conditions, display conditions, process conditions, various conditions for cells, temperature, pH, etc.) can be displayed in real time. The present invention may be equipped with a function of issuing an alarm when a temperature or pH departs from the tolerable range.

On a data analysis screen, it is possible to set conditions for various mathematical analyses, such as Fourier transformation, cluster analysis, FFT analysis, coherence analysis, correlation analysis, and the like. The present invention may be equipped with a function of temporarily displaying a profile, a function of displaying topography, or the like. The results of these analyses can be displayed while being superimposed with microscopic images stored in a recording medium.

In an embodiment, in the sensor of the present invention, the d) means for providing information comprises d-1) signal processing member for using a stimulus species categorizing method based on the stimulus element tuning specificity of a cell having a chemical receptor to add a first signal output by predetermined plurality of said sensors, to calculate a value of sensory elemental information expressing a sensation, and outputting a calculation result as a second signal; and d-2) evaluation member for effecting qualitative and/or quantitative evaluation using the second signal output by the signal processing member. Such means for providing information is described herein in detail elsewhere in the specification, and is enabled. It is currently possible to conduct quantitative or qualitative evaluation which was not achievable by the conventional methods, by conducting such information analysis. Preferably, the stimulus species categorizing method used in the aforesaid means for providing information advantageously uses classification according to the species of the chemical receptor. Classification allows more detailed or specific analysis.

In an embodiment, the signal processing member reduces as used in the present sensor, when one of first signals output by the plurality of sensors exceeds a predetermined value, the first signal output by a sensor different from the sensor and uses the reduced signal for producing the second signal. Such analysis allows more detailed analysis.

In another embodiment, the signal processing member used in the sensor of the present invention comprises: a plurality of selection members and addition members corresponding to sensory elemental information; a plurality of amplification members corresponding to each of the sensors; a coefficient calculation member for controlling the amplification member, wherein the selection members multiplies a plurality of the first signal with the coefficient designated by each of the sensors to produce a plurality of third signals; the addition members add the plurality of third signals output by the corresponding selection member to produce a plurality of fourth signal; the coefficient calculation member detects the maximum value among the plurality of fourth signals and normalizes each of the fourth signals using the maximum value to calculate control signals; the amplification members use the corresponding control signals to produce the second signals corresponding to the intensity of sensory elemental information. Such a step allows normalization of signals for presenting analyzed data such that subsequent analysis can be simplified.

In another embodiment, in the sensor of the present invention, when a stimulus such as a chemical including gustatory source, olfactory source and the like, is presented, the first signal output by the sensor, is transiently produced directed to a predetermined value corresponding to the intensity or concentration of the stimulus from zero level, wherein the zero level is set as a status where no response is found in response to no stimuli; the third signal is transiently produced associated therewith directing to a predetermined value corresponding to the intensity or concentration of a stimulus from zero level: the coefficient calculation member determines a sensor response starting at base time when one of the first signals is determined to be the signal output in response to a stimulus by the sensor for the first time, and calculates at a predetermined time as an elapsed time from the base time, the control signal for controlling the amplification member using the third signal at the predetermined time; controls the amplification member using the control signal which was calculated at the last time until a control signal is calculated at the predetermined time. Such a step allows more detailed analysis.

In another embodiment, in the present invention, when a stimulus such as olfactory sources and the like, is presented, the first signal output by the sensor, is transiently produced directed to predetermined value corresponding to the intensity or concentration of the stimulus from zero level, wherein the zero level is set as a status where no response is found in response to no stimuli; the third signal is transiently produced associated therewith directing to a predetermined value corresponding to the intensity or concentration of a stimulus from zero level; the coefficient calculation member determines a sensor response starting at base time when one of the first signals is determined to be the signal output in response to a stimulus by the sensor for the first time; during a period of time when the predetermined number of the plurality of third signals change from augmentation to reduction, and calculates, at each time when the third signal is determined to start occurring significant output as a corresponding sense element, and when the third signal is determined to have achieved a plurality of boundary values which divide the section between the significant output value and the maximum value preset to the third signal into a plurality of segments; controls the amplification member using the control signal which was calculated for the last time until the control signal is calculated. Such a step allows representation of more detailed analysis in a normalized manner.

In a further embodiment, a microfluidic chip for use in detecting odorant comprising a stabilized biologically-derived G-protein coupled receptor immobilized on a support, and arranged in at least two dimensional microarray system is provided. In one embodiment, the microfluidic chip can be disposable or non-disposable. A non-disposable microfluidic chip can be obtained by making the G-protein coupled receptor in situ and on demand from oligonucleotide sequences. The micro-well chip is regenerated by microfluidic channels after each reading either by washing each well and/or apply fresh G-protein coupled receptor for binding. The term "array" refers to a substrate (e.g., a chip, etc.) which has a pattern of composition containing at least one (e.g., 1000 or more, etc.) target substances (e.g., DNA, proteins, transfection mixtures, etc.), which are arrayed. Among arrays, patterned substrates having a small size (e.g., 10×10 mm, etc.) are particularly referred to as microarrays.

The terms "microarray" and "array" are used interchangeably. Therefore, a patterned substrate having a larger size than that which is described above may be referred to as a microarray. For example, an array comprises a set of desired transfection mixtures fixed to a solid phase surface or a film thereof. In a preferred embodiment the number of sensors and size of the two dimensional microarray system of the microfluidic chip is selected from:

| total # of sensors | dimensions (mm) |
|---|---|
| 36 | 4 × 4 |
| 100 | 6 × 6 |
| 400 | 11 × 11 |
| 900 | 16 × 16 |

As used herein, the terms "chip" or "microchip" are used interchangeably to refer to a micro integrated circuit which has versatile functions and constitutes a portion of a system. Examples of a chip include, but are not limited to, DNA chips, protein chips, and the like. Chips may comprise tubing for supplying a solution. Such tubing may be made of any material as long as no adverse effect is given to the substance of interest in a sample of interest. When administering the stimulus as a solution, a flow rate may be about 1-4 mm/second, preferably about 2.5 mm/second so that cells are not affected by mechanical stimulation by hydraulic pressure, and the entire cell can receive the stimulus in a short period of time. When administering a stimulus in a gaseous form, a gas of interest is introduced into the center of the sensor in an array format. Such a method may be any known method in the art. As an example, the sensor member is enclosed, the exhaust pump is subjected to a weak negative pressure by connecting thereto, the opening of a tubing for introducing a gas of interest from outside is fixed to the vicinity of the sensor member, and when introducing a gas into a solution in which a cell is soaked, in order that a physical fluctuation arisen by wind to the water interface, does not give effects on a signal of interest, the liquid interface is maintained at place by subjecting glass cover onto the site of measure on a sensor array. The introduced gas may be equally distributed onto the sensor member by spraying the gas above the cell in a solution having no odor which soaks the cell and flows at a determined flow rate. Further, in another embodiment, it is possible that no glass cover is arranged onto the above of the sensor member and the introduced gas is directly subjected to the sensor array at a flow rate so that signals have no effects of water interface fluctuation by wind. In this instance, the water depth of the sensor member is about 1-2 mm and the sensor member may be in a condition where a solution should not repel from the sensor member by subjecting stimulus hydrophobic components to the sensor member. In order to maintain the cleanliness in the vicinity of a cell, twenty to thirty seconds after the measurement, it may be necessary to replace the solution in the vicinity with a solution without the chemical of interest.

In a further embodiment, a method of manipulating of the bubbles in complex microfluidic networks, wherein the bubbles travel in a microfluidic channel carrying a variety of gas samples to a precise location on a chip, thereby improving sensitivity and precision in odorant detection is provided.

Yet in another embodiment, method of fabricating hOR17-4 olfactory receptor using expression system selected from cell-free, bacteria (*E. coli*) and yeast is provided. Preferably the yeast expression system is *Pichia pastoris*. The term "cell" is herein used in its broadest sense in the art, referring to a structural unit of tissue of a multicellular organism, which is capable of self replicating, has genetic information and a mechanism for expressing it, and is surrounded by a membrane structure which isolates the cell from the outside. In one embodiment, cells used herein may be either naturally-occurring cells or artificially modified cells (e.g., fusion cells, genetically modified cells, etc.), as long as the cell has a chemical receptor or is capable of having such a chemical receptor introduced therein. Examples of cell sources include, but are not limited to, a single-cell culture; the embryo, blood, or body tissue of normally-grown transgenic animals; a mixture of cells derived from normally-grown cell lines; and the like. Preferably, a cell which is easily transformed or transfected is used. Cells used in the present invention are preferably cells which are easily cultured and/or maintained on a support. Cells used herein may be derived from any organism (e.g., any unicellular organisms (e.g., bacteria and yeast) or any multicellular organisms (e.g., animals (e.g., vertebrates and invertebrates), plants (e.g., monocotyledons and dicotyledons, etc.)). For example, cells used herein are derived from a vertebrate (e.g., Myxiniformes, Petronyzoniformes, Chondrichthyes, Osteichthyes, amphibian, reptilian, avian, mammalian, etc.), more preferably mammalian (e.g., monotremata, marsupialia, edentate, dermoptera, chiroptera, carnivore, insectivore, proboscidea, perissodactyla, artiodactyla, tubulidentata, pholidota, sirenia, cetacean, primates, rodentia, lagomorpha, etc.). In one embodiment, cells derived from Primates (e.g., chimpanzee, Japanese monkey, human) are used. Particularly, without limitation, cells derived from a human are used. The above-described cells may be either stem cells or somatic cells. Also, the cells may be adherent cells, suspended cells, tissue forming cells, and mixtures thereof. The cells may be used for transplantation.

Another embodiment includes a substrate with a cell located thereon, the cell having the nucleic acid molecule introduced (for example, by transformation, transduction, transfection and the like) therein, may be prepared by fixing the cell with the nucleic acid molecule introduced therein to a substrate, or introducing (for example, by transformation, transduction, transfection and the like) the nucleic acid molecule to a cell after the cell is fixed to a substrate. Cell as used herein may be any cell as long as the cell may express a nucleic acid introduced therein. Preferably, cells that can be easily maintained on a substrate are desirable. Such a cell may include, but is not limited to, for example, HEK293 (HEK293S), CHO, COS-7, neuroblastoma, NG108-15 and the like. Any substrate may be used with any material or form, as long as the substrate can be used as a sensor of the present invention. Preferably, the material is advantageously biocompatible. The sensor of the present invention uses a mechanism using expression sustaining biological activity of a chemical receptor in a cell, and therefore the survival of the cell is preferable. Accordingly, when no biocompatible material is used, it may be desirable to coat such a material with a biocompatible material. Preferable form may be for example, quadrangle such as square, as this form is amenable for normalization.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Protocols:

A) Fabrication (Purification) and Stabilization/Regeneration of ORs.

i) Expressing protein in bulk: Human embryonic kidney cell, *E-coli* and cell-free expression systems (CFES) for the expression and purification of large quantities of the human OR17-4 receptor have been studied. Protocols for expression, stabilization, solubilization, functional assays, binding/adsorption to a variety of surfaces, spectroscopic assays etc. have been developed that aim at the mass-production of this receptor. These protocols can be modified to fit other receptors.

This technology can be used to make disposable micro-well chips where each well contains a different smell receptor. Once the chip has been exposed to the gas/air of interest it is read and discarded.

ii) Making the smell receptors in situ and on demand from oligonucleotide sequences is another way to operate the smell sensor. In this case, the micro-well chip is not disposable but rather is regenerated by microfluidic channels after each reading either by washing each well and/or applying fresh smell receptors for binding. Preliminary experiments have been done expressing human olfactory receptors in-situ using a CFES kit as well as expressing GFP that has been shown to be functional upon microfluidic assisted expression.

Production of Human Smell Receptor in Cell Free Expression System

Genes coding for human smell receptor 17-4 (hOR17-4) and production constructs for expression in cell-free systems, bacteria (*E. coli*) and yeast have been molecular engineered using a high-cycle number PCR-based method of gene synthesis. This method has also enabled us to achieve optimal codon usage in the different production systems.

One advantage of using a cell free system for production of membrane proteins is that surfactants can be present during translation and folding of the protein. By using the constructs mentioned above, the optimal surfactant and surfactant concentration for production of soluble receptor has been identified. Interestingly the addition of a stabilizing peptide surfactants developed in our lab significantly enhanced production levels at least five fold. The receptor has been partially purified using affinity purification, based on a tag engineered to the N-terminal of the protein, and subsequently by size exclusion chromatography. The production is currently being scaled up and should result in enough receptor to start crystallisation trials and prototype sensing nanodevice chip fabrication.

It is known that production of membrane proteins in *E. coli* can result in membrane insertion or formation of inclusion bodies containing unfolded protein. To efficiently monitor expression yield and membrane insertion in vivo has green fluorescent protein (GFP) been fused to the C-terminal of the receptor, as GFP only emits green color when correctly folded, namely, not in inclusion bodies. The production of the smell receptor was optimized for signal sequence, culturing time, temperature and media. During the optimization phase we successfully increased the production yield of membrane inserted smell receptor up to 4 mg/L culture, a very good yield for such system.

Therefore the fluorescence from the smell receptor-GFP fusion has also been used for identifying a suitable surfactant for solubilization of the protein from the membrane. FC-14 is currently the most effective surfactant tested, it can solubilize up to ~95% of the receptor. In addition, using a microscope equipped with the correct filters we have been able to localize the expressed smell receptors to the cell membrane.

Large Scale Production of Smell Receptor in Yeast *Pichia pastoris* as Expression System The methylotrophic yeast *Pichia pastoris* has been used for many years for producing a wide range of recombinant proteins. This *Pichia pastoris* production system has a highly inducible promoter (methanol). Genomic integration of the production cassette has the advantage that the production vector will not be lost on induction. Yeast *Pichia pastoris* is particularly efficient, it grows rapidly, reaches high cell densities, does not make hyperglycosylation and possesses extremely efficient secretory machinery. Several similar receptors to smell receptors have been functionally produced in *Pichia pastoris*. Expression levels vary from 0.4-100 pmol/mg membrane proteins.

Production of Smell Receptor in *Pichia pastoris*

Our results showed that we could successfully produce the smell receptor hOR17-4 in *Pichia pastoris*. This is the first time, to our knowledge, that a smell receptor has been expressed in *Pichia pastoris*. We used 2 different vectors (Invitrogen, CA): pPICZ (with a signal sequence) and pPICZ (without signal sequence). Three different *Pichia pastoris* strains, X-33, KM71H and GS115, were transformed with both vectors respectively, resulting in six different clones containing the construct with an N-terminal His-tag for affinity purifications. Six different *Pichia pastoris* clones produced the smell receptor as detected by immunoblotting. Interestingly the wild type *Pichia pastoris* strain X-33, which produced the receptor with a signal sequence (for targeting to the membrane) showed the highest production level. Optimization of the production by varying production conditions (e.g. induction time, induction temperature, methanol concentration, medium) made an additional 2-fold increase. Synergistic effects are currently investigated. The production level of the smell receptor is ~50 pmol/mg membrane protein. This is a high yield compared to production of similar proteins in *Pichia pastoris* (0.4-100 pmol/mg). As *Pichia pastoris* has been developed into a highly successful system for the large-scale production of recombinant proteins, thus production of large quantities of smell receptors is highly feasible.

Large-Scale Mammalian Cell Line Production of Smell Receptors

Optimization of the extraction procedure for smell receptors transiently produced in the mammalian cell line HEK293S. In 2006 the research was focused on several areas in order to enable the mass production of smell receptors. First, we have engineered and constructed new producer cell lines in which production of the smell receptor can be directly controlled (a so called "inducible" system). This allows large-scale cell culture batches to be grown and then, when desired, concerted production of fresh smell receptor to be induced in 100% of the cells, with minimal toxicity.

Figure 2A:
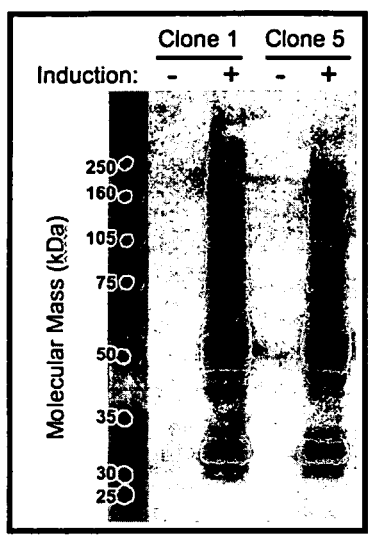
FIG. 2(a) Western blot of smell receptor purifications. There are two cell line clones, 1 and 5. – indicates no induction, + indicates inductions with tetracyclin/NaBu. The monomers and dimmers in both clones are clearly seen. The molecular size markers are on the left lane. (b) Inductions time with different concentration and combinations of tetracyclin/NaBu. The results clearly showed that 5 mM NaBu significantly enhanced the smell receptor production.
Figure 2B:
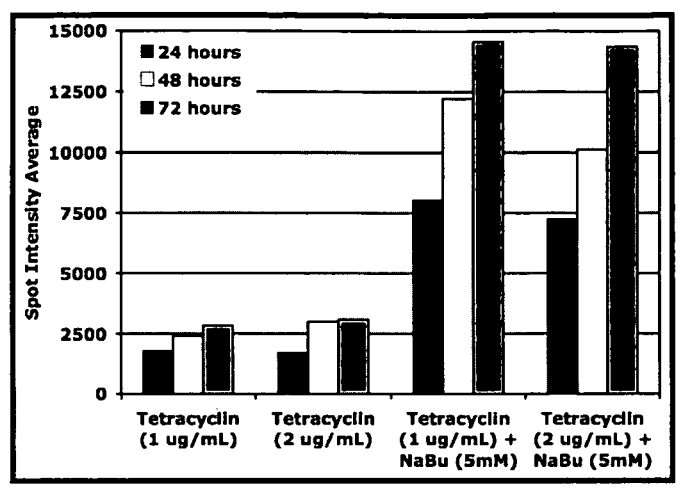

To obtain the highest amount of quality smell receptors, we have also optimized the induction protocol for each cell line generated with respect to time, concentration of inducer (tetracycline), and addition of a synergistic enhancer (sodium butyrate=NaBu). The results of the optimization are shown in FIG. 2.

Figure 3:
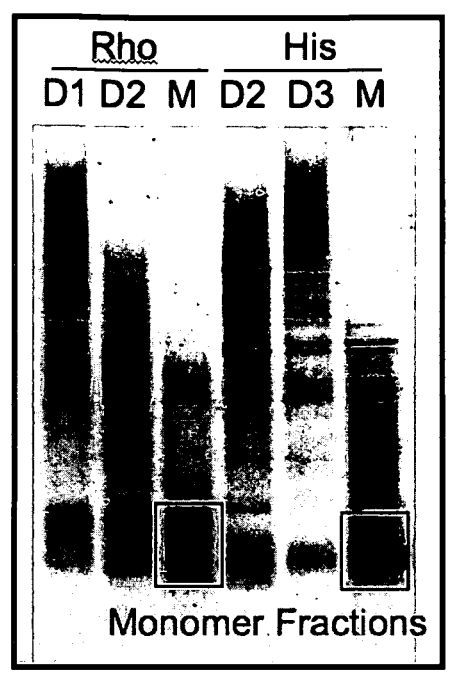
FIG. 3 illustrates smell receptor purification and examines its purity using gel electrophoresis. Two different purification Tags were used. Both Tags work well. M denotes monomer receptor, D denote dimmer protein fractions.

Using this protocol, we carried out a medium-scale purification trial on two versions of the smell receptor hOR17-4. The first version (hOR17-4-Rho) uses the "Rho" affinity tag at the C-terminus of the protein while the second (HF-hOR17-4) uses the "His" affinity tag at the N-terminus. Each smell receptor version was separately extracted, solubilized and purified using affinity-based chromatography. Additionally, we have now incorporated the use of a second purification step, gel filtration chromatography, to further polish the final product to a highly pure monomeric form (see FIG. 3). Using this method we successfully purified 0.13 mg of hOR17-4-Rho to >90% purity and 0.39 mg of HF-hOR17-4 to >70% purity.

We have begun using purified smell receptors for crystallization, a necessary step to obtaining high-resolution structural data using X-ray crystallography. Additionally, we will be using this purified smell receptor in newly devised experiments testing for stability, functionality and odorant binding. These experiments rely on fluorescence spectroscopy, Circular Dichroism, Biacore (also called Surface Plasmon Resonance), and single-molecule microscopy. The experimental results will be summarized in the future reports.

In order to complete our scale-up operation, we will be converting the system over from adherent culture plates to a large volume (5-10 liter) liquid bioreactor. In this system, our same inducible cells will be grown in fluid suspension to extremely high densities. This will allow the production and subsequent purification of milligram quantities of smell receptors necessary for all future experiments.

Fabrication (Purification) and Stabilization/Regeneration of ORs i) Expressing protein in bulk: Human embryonic kidney cell, E-coli and cell-free expression systems (CFES) for the expression and purification of large quantities of the human OR17-4 receptor have been studied. Protocols for expression, stabilization, solubilization, functional assays, binding/adsorption to a variety of surfaces, spectroscopic assays etc. have been developed that aim at the mass-production of this receptor. These protocols can be modified to fit other receptors.

This technology can be used to make disposable micro-well chips where each well contains a different smell receptor. Once the chip has been exposed to the gas/air of interest it is read and discarded.

ii) Making the smell receptors in situ and on demand from oligonucleotide sequences is another way to operate the smell sensor. In this case, the micro-well chip is not disposable but rather is regenerated by microfluidic channels after each reading either by washing each well and/or applying fresh smell receptors for binding. Preliminary experiments have been done expressing human olfactory receptors in-situ using a CFES kit as well as expressing GFP that has been shown to be functional upon microfluidic assisted expression.

Smell Receptor Gene Fabrication

To adapt the olfactory receptor genes (such as hOR17-4) for use in mammalian cell expression and purification, the following sequence modifications were made using the DNAWorks3.0 software (http://helixweb.nih.gov/dnaworks):

i. Human codon optimization
ii. Addition of C-terminal rho1D4 epitope tag "TETSQVAPA" (preceded by a two glycine linker) to facilitate purification
iii. Addition of NotI restriction site at 3' end of gene
iv. Addition of EcoRI restriction site and Kozak sequence (GCCACCACC) at 5' end of gene.

The designed oligos were purchased from IDT (Coralville, Iowa) with a maximum length of 45 bp. The assembly PCR was run for 45 cycles (much higher than the normal 25-30 cycles, the key for our success) using a mixture of all oligo DNA at a concentration of 25 nM each. The amplification PCR was run for 30 cycles using 1 µl of the assembly PCR (in a total reaction volume of 50 µl) and each end oligo at a concentration of 300 nM each. PCR reactions were then analyzed by gel electrophoresis and stained with ethidium bromide. Full-length product was exised, extracted, and then digested with the pertinent restriction enzymes. The genes were then ligated into the T-REx pcDNA4/To inducible expression plasmid (Invitrogen, Carlsbad, Calif.), sequenced, and a correct clones grown up using a MaxiPrep kit (Qiagen, Valencia, Calif.). The plasmid containing the optimized hOR17-4 gene was designated pcDNA4/To-hOR17-4rho.

Inducible Cell Line Generation

HEK293S (suspension adapted HEK293 cells) containing the stable expression of pcDNA6/Tr (Invitrogen), which encodes the Tet repressor protein (TetR) had previously been generated and cloned. The pcDNA4/To-hOR17-4rho plasmid was then transfected into these cells using Lipofectamine 2000 (Invitrogen) and after 48 hours cells were subjected to drug selection in 5 µg/ml blasticidin and 250 µg/ml zeocin for 2 weeks and then subcloned. Colonies were expanded and screened for inducible expression using tetracycline (1 µg/ml) alone as well as tetracycline plus sodium butyrate (5 mM, from Sigma) for 48 hours. Samples were then scrape harvested, solubilized in phosphate buffered saline (PBS) with 2% w/v Fos-Choline-14 (Anatrace, Maumee, Ohio) and Complete Protease Inhibitor Cocktail (Roche, Basel, CH) for 1 hour at 4° C. Expression was assayed via dot blotting and SDS-PAGE western blotting using the mouse monoclonal antibody □1D4. The colony showing the best expression of hOR17-4rho under induction conditions while maintaining undetectable expression without induction was chosen and expanded into large-scale culture. The hOR17-4rho inducible line was designated HEK293S rho5 and were maintained 5 µg/ml blasticidin and 250 µg/ml zeocin.

Smell Receptor Protein Purification

For initial small-scale experiments, 150 mm tissue culture plates were used per condition. Briefly, HEK293S rho5 cells were seeded at a density of $5 \times 10^6$ cells per 150 mm dish and grown for 72 hours at 37° C., at which point they reached 80-90% confluency. The cells were then induced with medium containing tetracycline (1 µg/ml) plus sodium butyrate (5 mM). After 24-40 hours, the cells were harvested by scraping (at 4° C.) each plate into 2 ml PBS containing Complete Protease Inhibitor Cocktail. The cells were then snap frozen in liquid nitrogen and stored at −80° C. until purification was carried out. For purification, cells were thawed on wet ice and spun down by centrifugation at 2000 rpm for 1 minute. All further steps were performed at 4° C. unless noted. The membrane proteins were then solubilized by resuspending the cells (1-2 ml per 150 mm plate) in PBS with 2% w/v Fos-Choline-14 and Complete Protease Inhibitor Cocktail and rotating for 4 hours. The non-solubilized fraction was then pelleted using an ultracentrifuge at >100,000 g for 30 minutes. The resulting supernatant was removed and stored at 4° C. A small amount of supernatant (100 µl) was set aside, labeled "total lysate" and stored at −20° C.

For immunoaffinity purification, the remaining supernatant was then mixed with 1D4-coupled sepharose bead slurry (50 uL per 150 mm plate) and rotated overnight to capture the tagged olfactory receptors. The beads were then pelleted by centrifugation at 2000 rpm for one minute and the supernatant collected, labeled as "flow-through" and stored at −20° C. The beads were then washed five times with 100× bead volume with wash buffer (PBS+0.2% Fos-Choline-14), and 100 µl of each sequential wash was saved, labeled, and stored at −20° C. After the final wash, the beads were pelleted again and transferred to a new tube for elution. Five 1-hour elutions were then carried out, each using 1× bead volume elution buffer (PBS+0.2% DM+100 µM TETSQVAPA (SEQ ID NO. 43) peptide), and each elution fraction was in turn labeled and stored at −20° C.

For further purification, hOR17-4rho proteins were subjected to gel filtration chromatography using a HiLoad 16/60 Superdex 200 column on an Akta Purifier system (GE Healthcare). The column was first equilibrated using wash buffer (PBS+0.2% w/v Fos-Choline-14). Pooled elution fractions from the 1D4 immunoaffinity purification concentrated to less than 500 µl using 10 kD MWCO filter columns (Millipore) and then applied to the Akta system. After loading, column was run with wash buffer at 1 ml/min and protein fractions collected and monitored with the UV detector at 215 and 280 nm.

Collected fractions were assayed via dot blotting or polyacrylamide gel electrophoresis (SDS-PAGE) under reducing and denaturing conditions. SDS-PAGE gels were run in tandem with one being used for total protein staining using SYPRO-Ruby (a more sensitive alternative to Coomassie; Invitrogen) and the other transferred to a 0.45 µm nitrocellulose membrane and subjected to western immunoblotting using the 1D4 as primary antibody, followed by secondary (goat anti-mouse HRP), and ECL-Plus Kit detection.

The method of purification was adapted from that described for rhodopsin. For further details concerning these protocols (as well as cell culture and bioreactor conditions), please see the following:

Reeves P J, Kim J M, and Khorana H G. (2002) Structure and function in rhodopsin: a tetracycline-inducible system in stable mammalian cell lines for high-level expression of opsin mutants. *Proc Natl Acad Sci* 99, 13413-13418.

Reeves P J, Thurmond R L, and Khorana H G. (1996) Structure and function in rhodopsin: high-level expression of a synthetic bovine opsin gene and its mutants in stable mammalian cell lines. *Proc Natl Acad Sci* 93, 11487-11492.

Protocol for Production of Olfactory Receptor hOR17-4 in Yeast *Pichia pastoris*

Materials
Invitrogen EasySelect™ *Pichia* Expression Kit (Invitrogen, Carlsbad, Calif.).
Oligonucleotides were from Integrated DNA technologies, (Coralville, Iowa)
TOPO cloning reaction kit (Invitrogen, Carlsbad, Calif.)
Complete protease inhibitors (Roche)
Fos-choline 14 (Anatrace, Maumee, Ohio)
Methods
Cloning The gene coding for olfactory receptor with an N-terminal his tag was assembled from oligonucleotides using gene assembling technique through PCR. The oligonucleotides were designed using DNA works (http://molbio.info.nih.gov/dnaworks).

Two restriction sites, EcoRI and XbaI were included in the design of the gene to allow cloning of the gene into pPICZ-A at a later stage. After assembling of the gene, it was cloned into pCRII-blunt-TOPO vector using the TOPO cloning reaction kit. After the gene was cloned into pPICZ-A *Pichia* expression vector. The wild-type *Pichia* strain X-33 was transformed using electroporation.

Expression of hOR17-4

Before induction, biomass of the transformed *P. pastoris* X-33 was accumulated by growing in BMGY (1% (w/v) yeast extract, 2% (w/v) peptone, 1% glycerol, 0.1 M phosphate buffer, pH 7.5) to an optical density (OD) of 2-6. Receptor expression was induced after elimination of medium by centrifugation (1000 g, 10 min) and addition of a buffered methanol-containing medium BMM to OD 1 (0.1 M phosphate buffer pH 7.5, 1.34% yeast nitrogen base, $4*10^{-5}$% biotin, 1% (v/v) methanol). After induction for 40 hrs at 30° C., cells were harvested by centrifugation and frozen at −80° C.

Isolation of Crude Membranes and Solubilization hOR17-4

Cells were thawed and were resuspended in breaking buffer (PBS, 5% glycerol, 1 mM EDTA, protease inhibitors) and were broken by French press, 3 runs at 30,000 Psi at 4° C. Unbroken cells and other larger cell material were eliminated by centrifugation (1,000 g, 10 min, 4° C.). Membranes were pelleted from the supernatant at 100,000 g for 45 min at 4° C., and resuspended in PBS with 2% Fos-choline 14 at 4° C. for 2 hrs.

Cell-Free Production for Smell Receptor 17-4

Materials
RTS proteomaster, Roche Diagnostics GmbH, Mannheim Germany
Wheat germ RTS 500 cell free expression kit, Roche Diagnostics GmbH, Mannheim Germany
Digitonin 10% solution, EMD Chemicals Inc, Darmstadt, Germany
Ac-A6D-COOH 1% solution,
hOR 17:4-Rho ORF in PIVEX expression plasmid from Roche Diagnostics GmbH, Mannheim
Smell Receptor Protein Production Procedure
Expression is set up according to Roche's manual and table I. Expression is performed at 24° C. for 24 hours at 900 rpm.

TABLE I

| Template | Reaction chamber | | Feeding chamber | |
| --- | --- | --- | --- | --- |
| 17-4 plasmid (µg) | detergent I | detergent II | detergent I | detergent II |
| 60 | Dig. (0.3%) | $A_6D$ (0.1%) | Dig. (0.3%) | $A_6D$ (0.1%) |

Purification of 17-4 from Cell-Free Lysate
Materials
Beads coupled with 1D4 antibody (Pharmacia Sepharose-4B, CNBr activated beads, GE Healthcare, Piscataway, N.J., USA
FC14, Anatrace, Maumee, Ohio, USA
Superdex 200 100/300, GE Healthcare, Piscataway, N.J., USA
ÄKTA purifier 10 chromatography system, GE Healthcare, Piscataway, N.J., USA
Centricon concentration devices, Millipore, Billerica, Mass., USA Protein Purification Procedure hOR17.4 purification should be started immediately after cell free expression is finished
1. Spin down pellet of unsolubilised material by centrifugation at 15,000×g for min;
2. Add the supernatant (900 ul from a 1 ml RTS 500 reaction) to 600 μl bead coupled with 1D4 antibodies directed against the Rho-tag and is incubated over night at 4° C.;
3. Spin the beads at 800×g for 1-2 min at 4° C.;
4. Remove supernatant;
5. Do 5 washes for 10 min each using 100 bed volumes each wash of PBS+10% glycerol+0.1% FC-14 (rotate at 4° C. during incubation, spin down beads between the washes);
6. Do five elutions of the receptor using one hour each using one bead volume of elution buffer (PBS+10% glycerol+0.1% FC-14+100 μM peptide (TETSQVAPA)—keep at ROOM TEMPERATURE (rotate at 4° C. during incubation, spin down beads between the elutions);
7. Concentrate the elution fractions to 600 μl using centricon concentration devices with a molecular cut off of 10000 kDa;
8. Apply 2×300 ul to a Superdex 200 100/300 column attached to a ÄKTA purifier 10 chromatography system equilibrated with PBS+10% glycerol+0.1% FC-14;
9. Collect fractions containing FC14 stabilized monomer at about 112 kDa. The receptor is 36 kDa and bound FC14 is calculated to 76 kDa, see FIG. 1.

Calcium-Influx Activity Assay

To determine if receptors expressed at the surface of induced HEK293S rho5 cells was functional, we performed calcium-influx assays. In our heterologous HEK293S system, olfactory receptors can signal through the inositol triphosphate (IP3) pathway to release intracellular Ca2+, using the "promiscuous" G-protein G☐q.

HEK293S rho5 cells were seeded and grown on glass coverslips until they reached 80-90% confluency. Expression of hOR17-4 was then induced with media containing tetracycline (1 μg/ml) for 48 hours. Cells were then washed with PBS and loaded with the calcium sensitive dye Fluo-3 (Invitrogen) according to the manufacturers instructions. Coverslips were then mounted and visualized using time-lapse confocal microscopy. Experiments were conducted in PBS and odorant stocks were added by hand using a pipettor to final concentrations between 1-100 μM. Both specific and non-specific odorants were tested. As an additional control to test whether cells could increase internal calcium levels, 1 mM ATP was added.

Protocol is adapted from:

Jacquier V, Pick H, and Vogel H. (2006) Characterization of an extended receptive ligand repertoire of the human olfactory receptor OR17-40 comprising structurally related compounds. *J Neurochem* 97, 537-544.

Functionality Smell Receptor Binding Determination Using Surface Plasmon Resonance One of the most important issues of smell receptor production is the functionality and the stability of the synthesized receptor. As there are no standard protocols to detect the interaction between odorant and solubilized smell receptor are we currently developing such a method using Surface Plasmon Resonance (SPR, Biacore instrument). The detection of the binding of the very small smell molecules, the odorants are usually smaller than 250 in molecular weight compared to the ~35,000 in molecular weight receptor, is a very big challenge but not impossible using SPR.

Our recent results showed that our produced receptor (from yeast and cell free) is still active after solubilization from the membrane using a phosphocholine (surfactant). This means that the receptor is not only produced in its functional form, but also it is still stable after the solubilization. Obviously, this result is a milestone in the development of the smell biosensor.

Currently, using a set of known agonists and antagonist, as well as non-binding smell molecules, we are investigating the binding of different smell receptors to smell receptors, both qualitatively and quantitatively.

Figure 4:
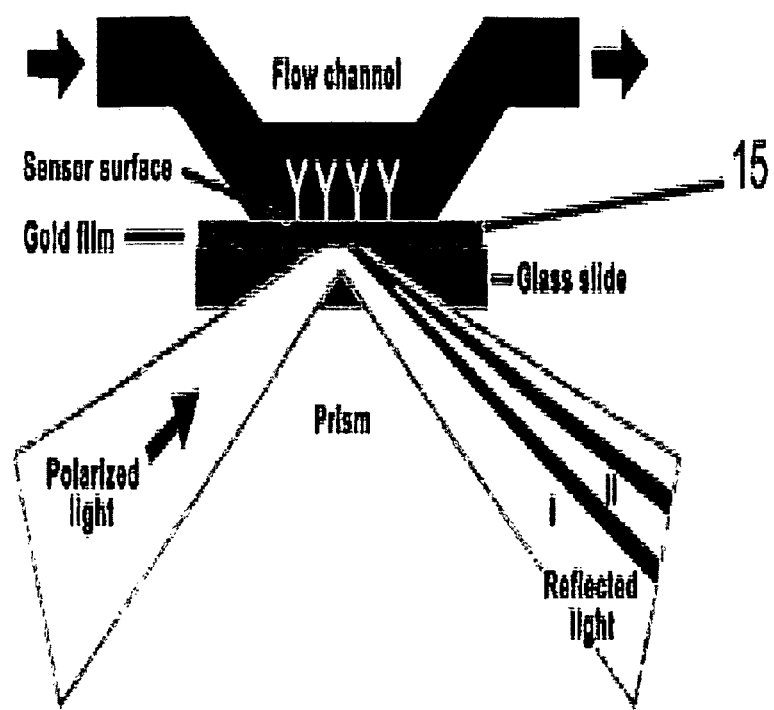
FIG. 4 illustrates physics, optics and chemistry of how Surface Plasmon Resonance works. Binding of smell molecules (red) to a smell receptor (Y) using Surface Plasmon Resonance. This system can be made into an array with thousands of receptors on a biotech chip.
Figure 5:
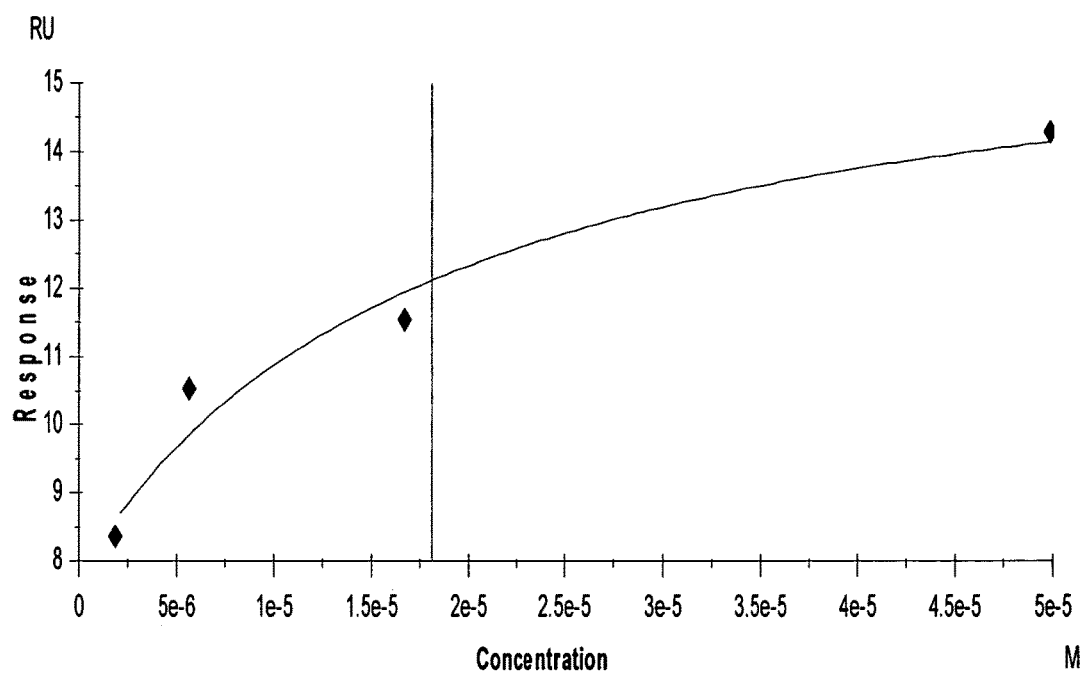
FIG. 5 represents a graph of measured binding of a smell molecule to the smell receptor hOR17-4. The graph shows a dose-response curve indicative of specific interaction between the smell molecule and the receptor. The vertical bar indicates the calculated affinity constant (16 μM).

Stabilization of the Olfactory Receptors in Solution Using Different Chemical Surfactants and Peptide Surfactants Previous work of our lab has successfully kept membrane proteins functionally stable in both wet (aqueous) and dry states for several weeks with the use of the peptide surfactants $A_6K$, $A_6D$ and $V_6D$. In year 2007-2008, we will use SPR for detection of smell molecules in a SPR based biosensor using an array of receptors from different species and different types of smell molecules. A conceptual embodiment of an SPR sensor is shown in FIG. 4 to illustrate the underlying principles. A sample interaction of a smell molecule and the receptor found on the SPR sensor are shown in FIG. 5. It should be noted that SPR could be miniaturized for the smell receptor based biosensing nanodevice.

Structural Determination of the Smell Receptors

Understanding the functional mechanism of olfactory receptors can only be achieved through detailed structural analysis. Considerable evidence suggests that the surfactant peptides will facilitate the crystallization of purified olfactory receptors for X-ray diffraction and may additionally enable the use of both solution and solid-state NMR spectroscopy. In order to perform these studies we need milligram quantities of purified receptors. We currently have stocks prepared from a large-scale production, enough receptor for crystal screenings. This automated screen tests >2000 separate crystallization conditions and results will be applied to crystallizations for completely X-ray diffraction studies. As soon as we have good crystals, we will determine its detailed molecular structure.

Testing the Vibrational Theory of Olfaction Using Scanning Tunneling Microscopy (STM)

The dominant theory of olfaction is that the shape of the odorant molecule is what olfactory receptors recognize. This theory is problematic because molecules that are shaped exactly alike (for instance an odorant with all its hydrogen atoms replaced by deuterium ones) not only smell different[3], but also give different neural activation patterns. On the other hand, structurally unrelated molecules smell alike (a well-known example is the at least 75 dissimilar shaped molecules—all smelling of bitter almond).

One hypothesis, the "vibrational theory of smell", postulates that when an appropriate odorant molecule binds to an olfactory receptor protein electrical conductance through the receptor increases, activating an intricate biochemical and neural pathway, which ultimately results in the conscious perception of an odor. Although the biochemical aspects of this are well documented, the first step—a local change in conductance—is yet determined.

The most direct way to test the vibrational theory of smell is the method as follows: immobilize an olfactory receptor, in its active form, in a scanning-tunneling microscopy (STM) chamber and measure the efficiency of electron tunneling before and after the receptor is exposed to its odorant. If there is a significant increase in the tunneling efficiency when the receptor has bound its odorant, versus when it is exposed to random odorants, we will have the first ever evidence for the vibrational theory of smell. With this method we will be addressing single molecules in a highly controlled environment.

The most important problem is that the olfactory receptor protein, being a membrane protein, is sensitive and unstable, extremely hard to produce, and nearly impossible to keep functional in unnatural environments such as the insides of an STM chamber. However, in our laboratory we have succeeded in keeping similar proteins (of the G-Protein Coupled Receptor—GPCR family) functional by using custom-designed surfactant peptides to play the role of their natural lipid bilayer environment.

The second problem is assaying that we have a layer of immobilized olfactory receptors on a conducting surface. Following protocols for immobilizing other GPCRs, we have started using SPR to monitor immobilization of monolayers.

We have already confirmed that proteins work well for STM. We have started experimenting with Carbonic-anhydrase protein immobilized on platinum electrodes to understand the thermal and other behavior before we use actual olfactory receptors, which are much harder to obtain.

Surface Plasmon Resonance of Odorant Binding to Smell Receptor

Materials

Figure 6:
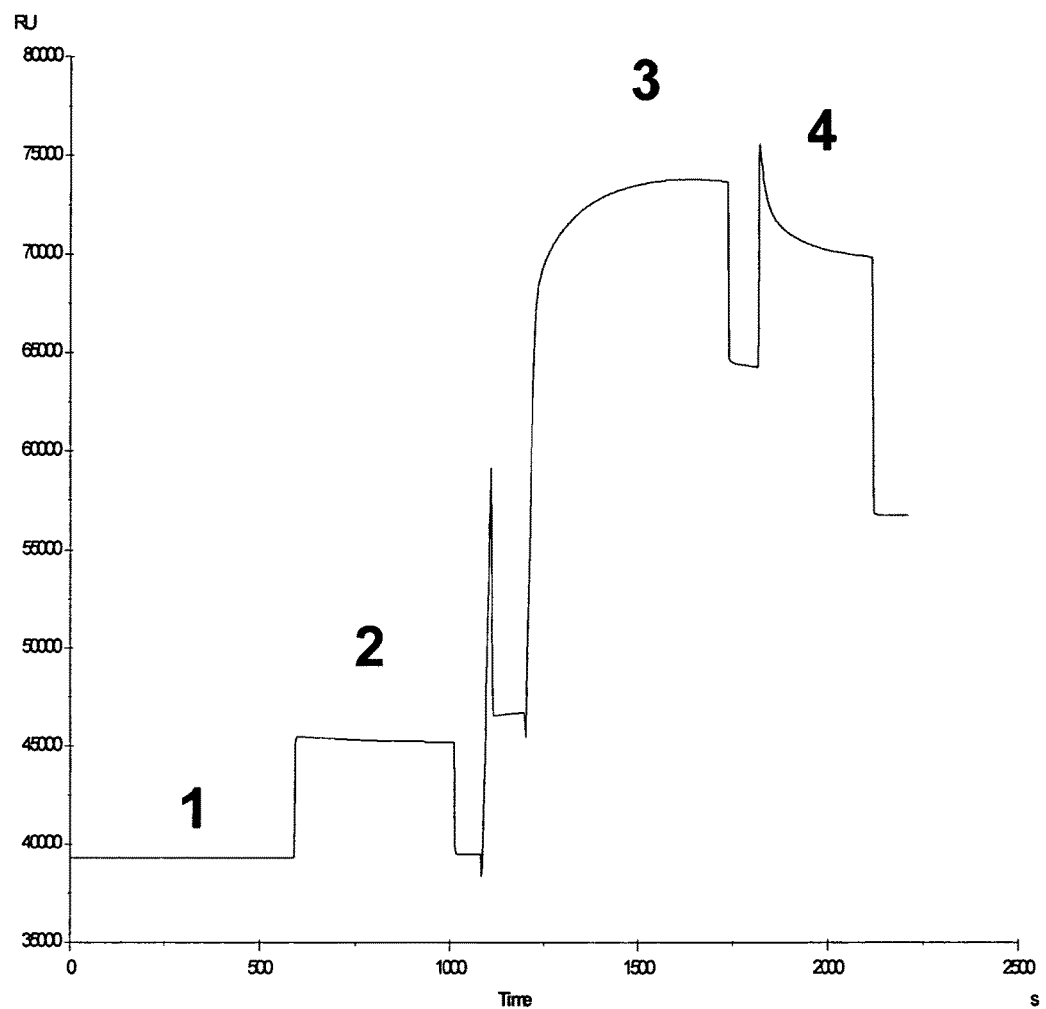
FIG. 6 represents a surface Plasmon resonance graph of the immobilization of ID4 antibody: (1) Running buffer: HBS, flow rate 10 ml/min. (2) Surface activation: Amine coupling: 7-min injection of a 1:1 ratio of 0.4M EDC/0.1M NHS. (3) Immobilization: 3-min injection of 0.05 mg/ml ID4 in 10 mM sodium acetate pH 5.5. (4) Deactivation: 7-min injection 1 M ethanolamine.
Figure 7:
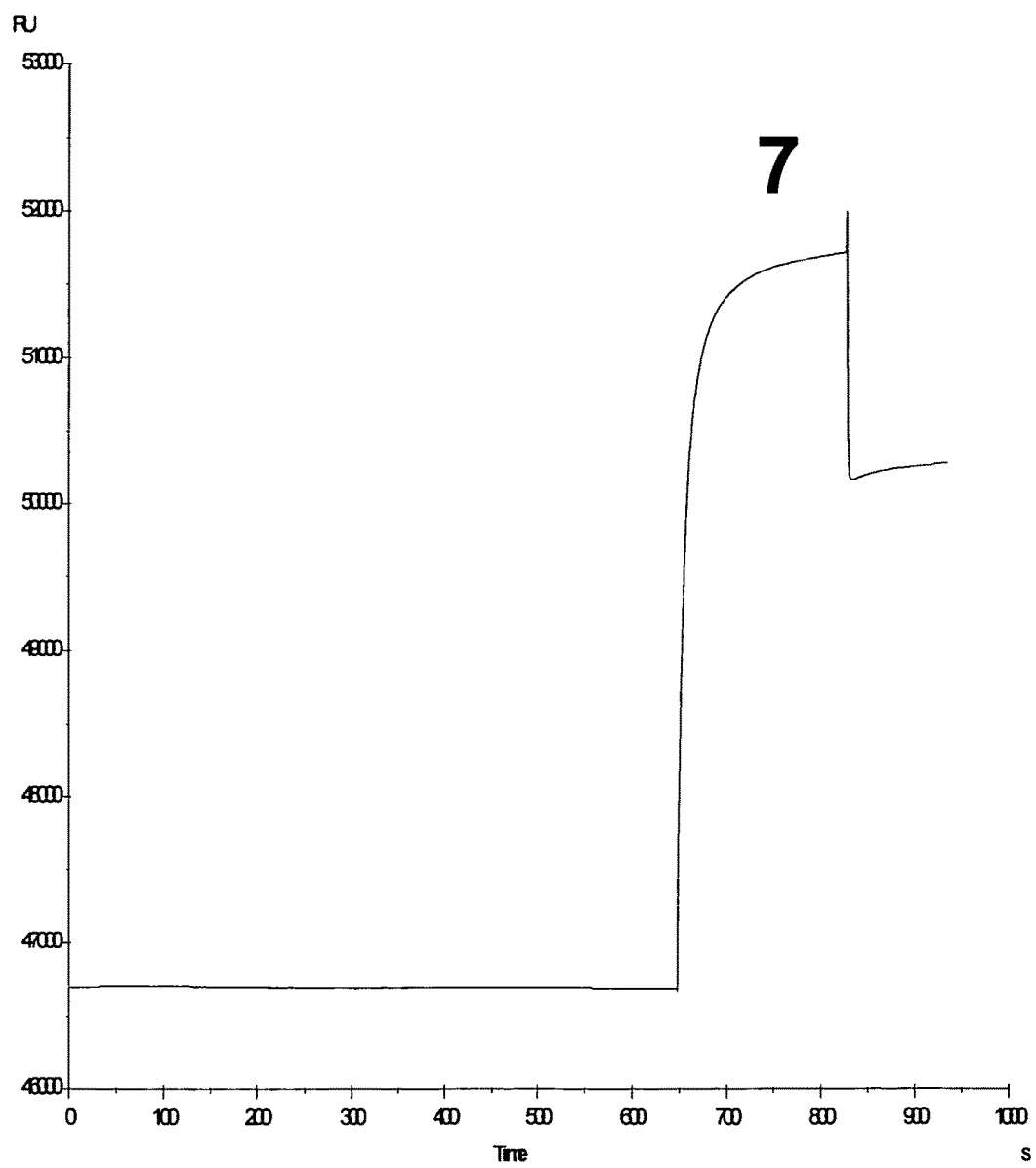
FIG. 7 shows a surface Plasmon resonance graph of the capturing of the olfactory receptor hOR17-4.
Figure 8:
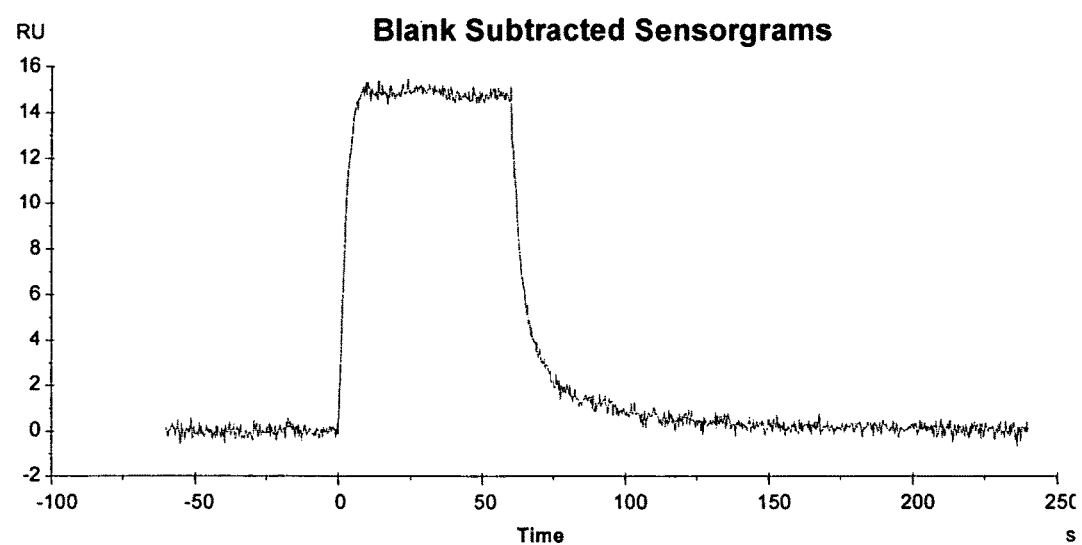
FIG. 8 shows a ligand binding diagram.

Biacore system: T100 and A100
Biasensor chip CM4 (carboxylated dextran immobilized on Au) (Biacore)
EDC: ethyl-3-(3-dimethylaminopropyl) carbodiimide hydrochloride (Biacore)
NHS: N-hydroxy succinimide (Biacore)
Ethanolamine (Biacore)
PBS: 10 mM phosphate buffer pH 7.4; 2.3 mM KCl; 0.137 M NaCl (Biacore)
HBS: 10 mM Hepes pH 7.4; 0.15M NaCl (Biacore)
ID4 antibody (Cell essentials, Boston Mass.)
Ethanol
Floralozone (Flavor Sciences, Stamford Conn.)
Immobilization of ID4 Antibody (see FIG. 6)
1. Running buffer: HBS, flow rate 10 ml/min.
2. Surface activation: Amine coupling: 7-min injection of a 1:1 ratio of 0.4M EDC/0.1M NHS.
3. Immobilization: 3-min injection of 0.05 mg/ml ID4 in 10 mM sodium acetate pH 5.5.
4. Deactivation: 7-min injection 1 M ethanolamine.
Capture of Olfactory Receptor hOR17-4 (see FIG. 7)
5. Change buffer: PBS, 0.1% (w/v) CHAPS/0.05% CHS/ 01% DDM, 1% (v/v) ethanol. Flow rate 10 µl/min
6. 2× priming of system
7. Capture of olfactory receptor: 3-min injection of hOR17-4 from cell free expression
Ligand Binding (see FIG. 8)

Injection of odorant solution: contact time 60 s; flow rate 80 µl/min; dissociation time 120 s. Injection of at least 5 different concentrations (1-100 µM, injection from low to high concentration). Preparation of odorant solution: fresh 50 mM stock solution in 100% ethanol, then further dilutions in running buffer.

Highly Parallel Receptor-Ligant Interaction Detection System

The goal of this project is to be able to detect a measurable change in the nuclear-magnetic resonance spectrum of the binding of a ligant (smell source or other small molecule) to a receptor protein. The proposal is to create a parallel array of microslot devices [1] which will be able to collect information on these proteins in parallel. The microslot is a recent innovation to improve the sensitivity of magnetic resonance for detecting small quantities of protein. In [1], it was experimentally shows that $10^{14}$ molecules (1.57 nanomoles) of ribonuclease-A in 188 mL of solution could be measured using this technique.

Figure 9:
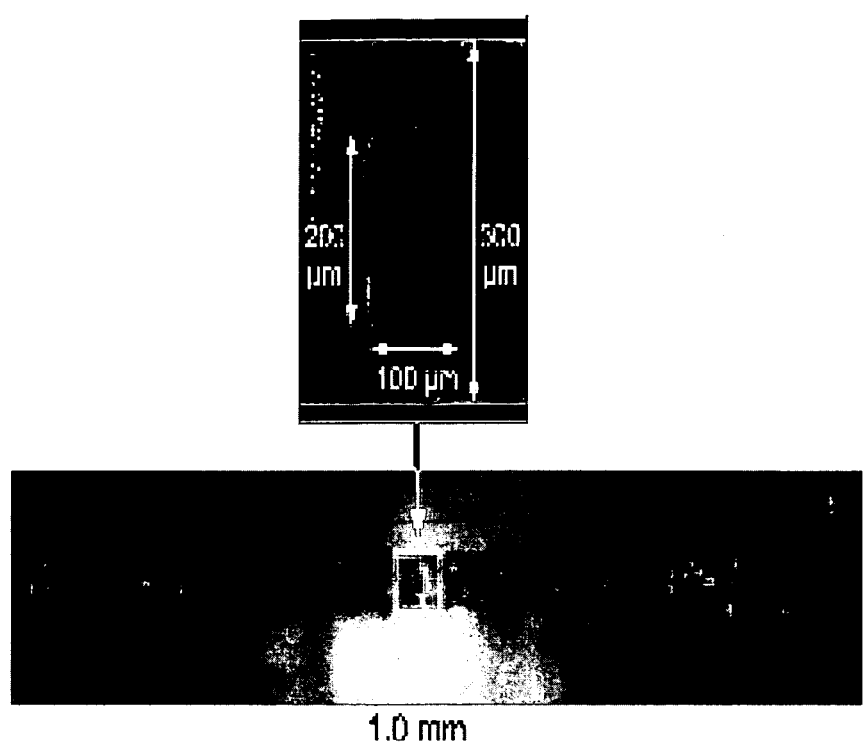
FIG. 9 is a depiction of a microslot probe.
Figure 10A:
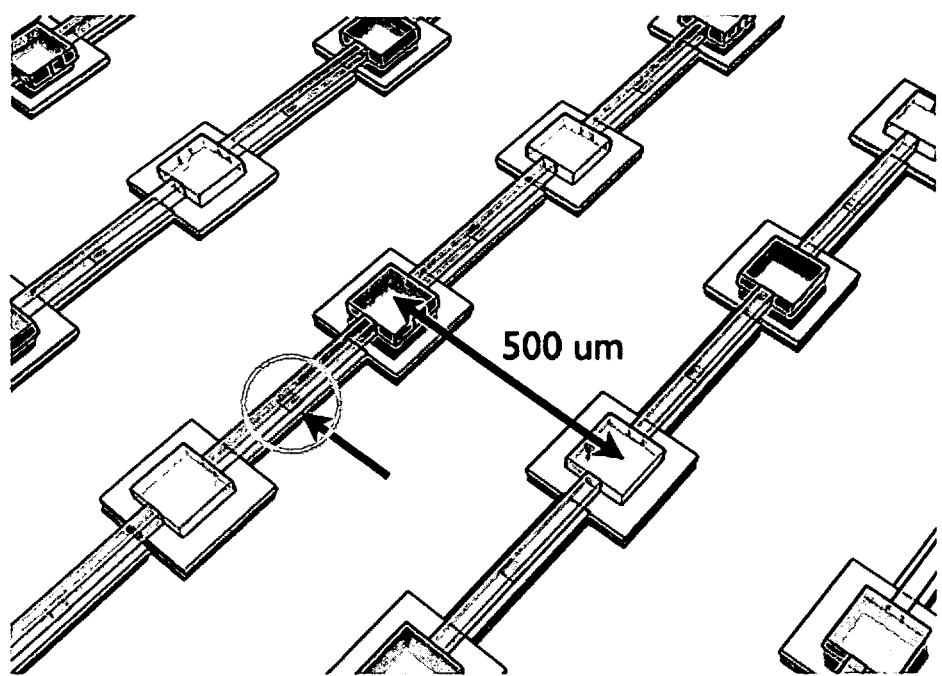
FIG. 10 (a) a close up of the detector element shown with a microfluidic network placed on top, (b) a schematic of a 4×4 mm chip which contains 36 sensors.
Figure 10B:
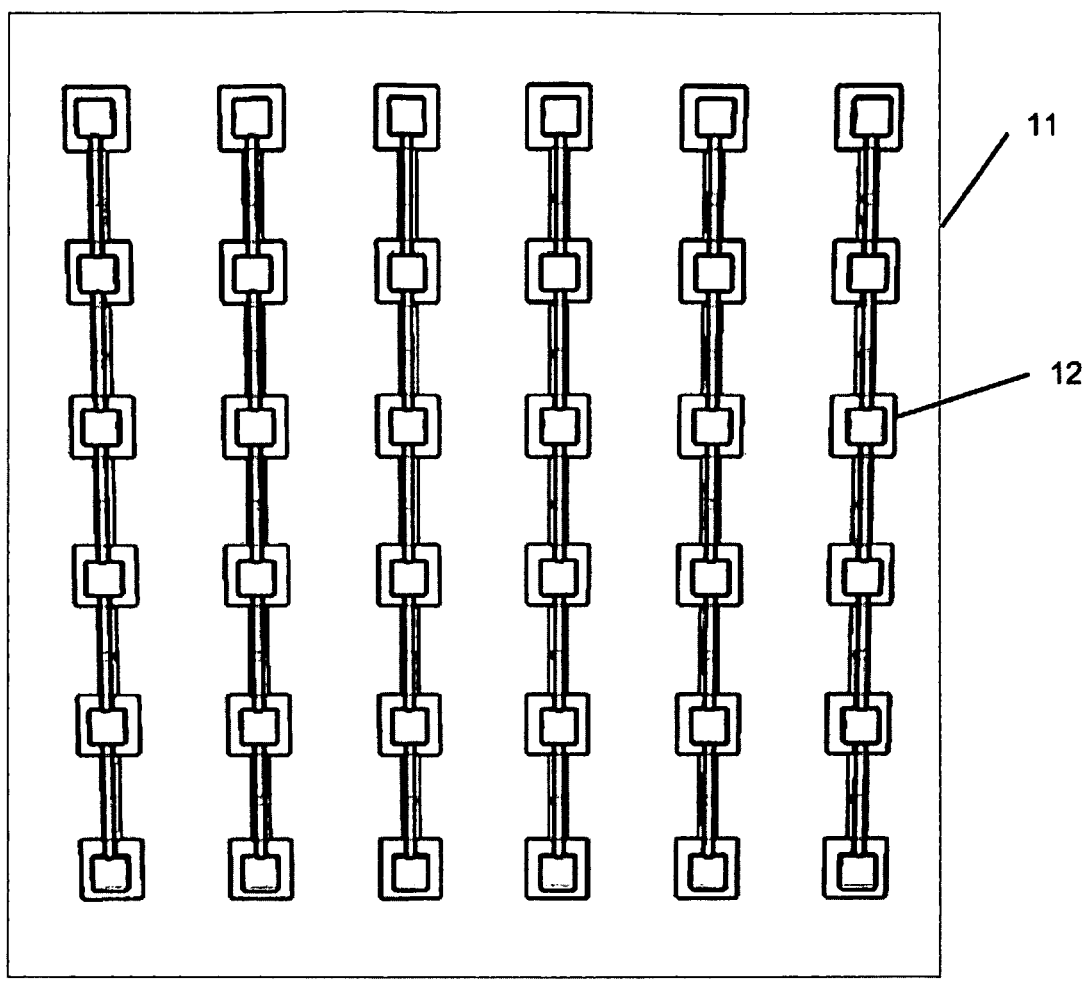

The microslot probe (FIG. 9) was manufactured using conventional circuit board fabrication techniques followed by a fast post-processing step using an excimer laser which is a highly automated, fast and inexpensive technique. One of the features of this design is that is can be highly parallelized. A visualization of this is shown in FIGS. 10 (a) and (b). The image on the left shows a close up of the detector element shown in the figure above with a microfluidic network placed on top. The image to the right of that is a schematic of a 4×4 mm chip which contains 36 sensors. The size of the sensor for N elements is 0.5 mm×N+1 mm by 0.5 mm×N+1 mm. A table of this is shown below:

| total # of sensors | dimensions (mm) |
|---|---|
| 36 | 4 × 4 |
| 100 | 6 × 6 |
| 400 | 11 × 11 |
| 900 | 16 × 16 |

The current specifications of each sensor:

984 µmul/Hz$^{1/2}$ at 600 MHz. This scales at $B_0^{7/4}$ with magnetic field strength. This allows 1D spectral determination of $10^{14}$ molecules in up to 200 nL of solution.

Estimated Cost of the Sensor

The microslot can be manufactured for less than $10, even in volumes under 1000 devices. The complex, but solely an engineering challenge, is creating the parallel processing for measuring all the NMR signals at radio frequencies. This is a novel piece of technology since a conventional spectrometer is designed to handle a single sample at a time. The estimated cost of the chip to enable this application is under $100 in small quantities given the current technology available from the cellular and WiFi industry and could go to less than $10 with volume.

REFERENCES

Yael Maguire, Isaac L. Chuang, Shuguang Zhang, and Neil Gershenfeld. Ultra-small-sample molecular structure detection using microslot waveguide nuclear spin resonance. Proceedings of the National Academy of Sciences. pp. 9198-9203. v. 204, no. 22. May, 2007, which hereby incorporated by its entirety.

Microfluidic Integration of Olfactory Receptors and Gas Delivery for Bio-Sensing Nanodevice Complex odorant cocktails require a combinatorics approach for detection. Thus a regulated mechanism for exposure of olfactory receptors to test sample is necessary. Receptors on the membrane, sit inside a mucus layer. This thin fluid film is necessary for stability of olfactory receptors in the membrane. The electronic nose needs to imitate such a gas-liquid transport mechanism. For sensitive detection of and fast rejuvenation of olfactory receptors, controlled exposure time to a variety of gas samples is necessary. Increasing the surface area to volume ratio of gas samples by using nano-liter volume bubbles, allows for fast diffusion of odorant molecule into the ambient fluid, improving device sensitivity. For e.g. a single odorant molecule would take seconds to diffuse to the surface for 1 ml gas sample, while it would take µ seconds to diffuse to a surface of 1 nl bubble.

This requires breaking down a test sample into nanoliter bubbles at high frequency. Control of routing of packets of gas bubbles in a microfluidic chip allows us to implement complex detection schemes. We have invented a new family of generalized tools for manipulation of bubbles in complex microfluidic networks. "Bubble Logic" employs micron-sized (nanoliters) droplets and bubbles of chemicals to mimic the actions of the electrons moving through the circuits of a microprocessor. A single bubble represents a bit. Now bits can simultaneously represent and manipulate materials and information. This new paradigm merges chemistry with computation. We have already demonstrated numerous digital logic components employing nanoliter volume bubbles in microfluidic networks; including AND-OR-NOT gates, flip-flops, ripple-counters, constant frequency bubble generators, modulators and ring oscillators. Thus bubbles traveling in a microfluidic channel can carry a variety of gas samples to precise locations on a chip. They can be stored in memory elements, routed on-chip, merged or split and transported at high throughputs.

Figure 11:
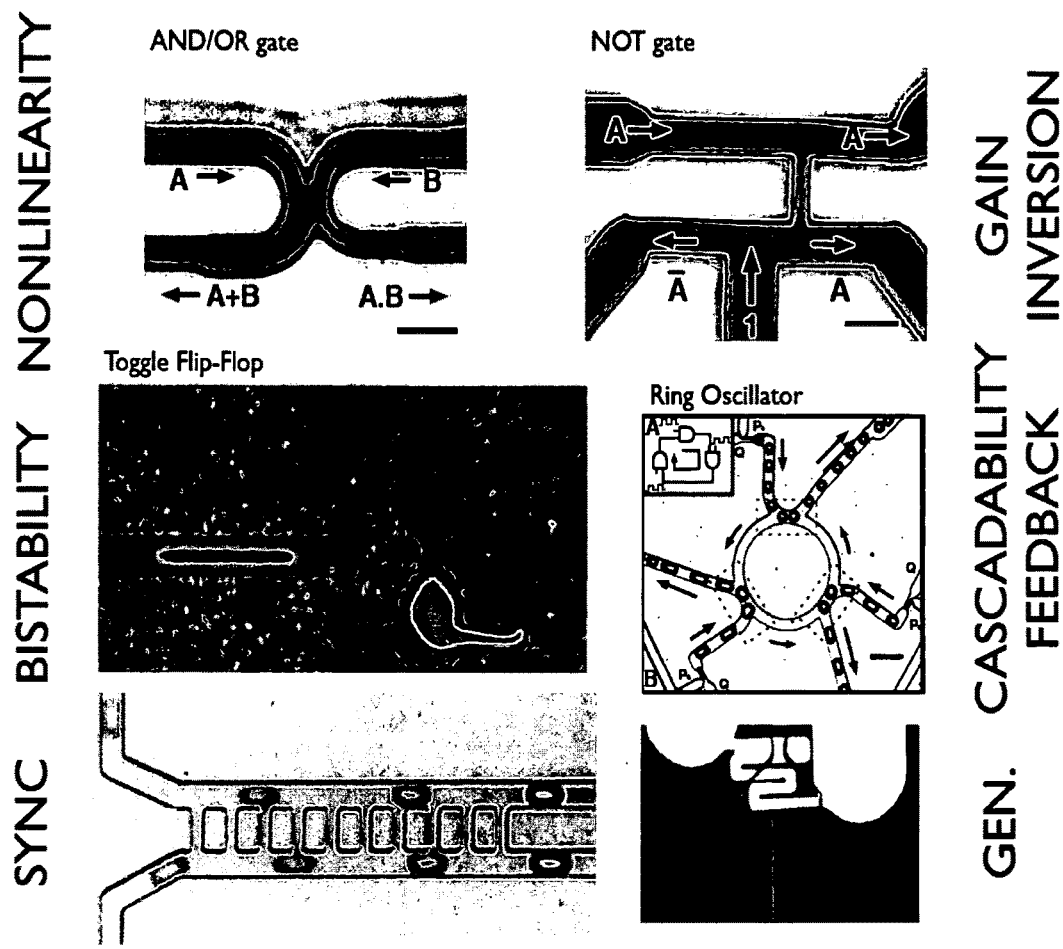
FIG. 11 illustrates numerous digital logic components employing nanoliter volume bubbles in microfluidic networks; including AND-OR-NOT gates, flip-flops, ripple-counters, constant frequency bubble generators, modulators and ring oscillators.

As shown in FIG. 11, numerous digital logic components employing nanoliter volume bubbles in microfluidic networks are possible; including AND-OR-NOT gates, flip-flops, ripple-counters, constant frequency bubble generators, modulators and ring oscillators.

Figure 12:
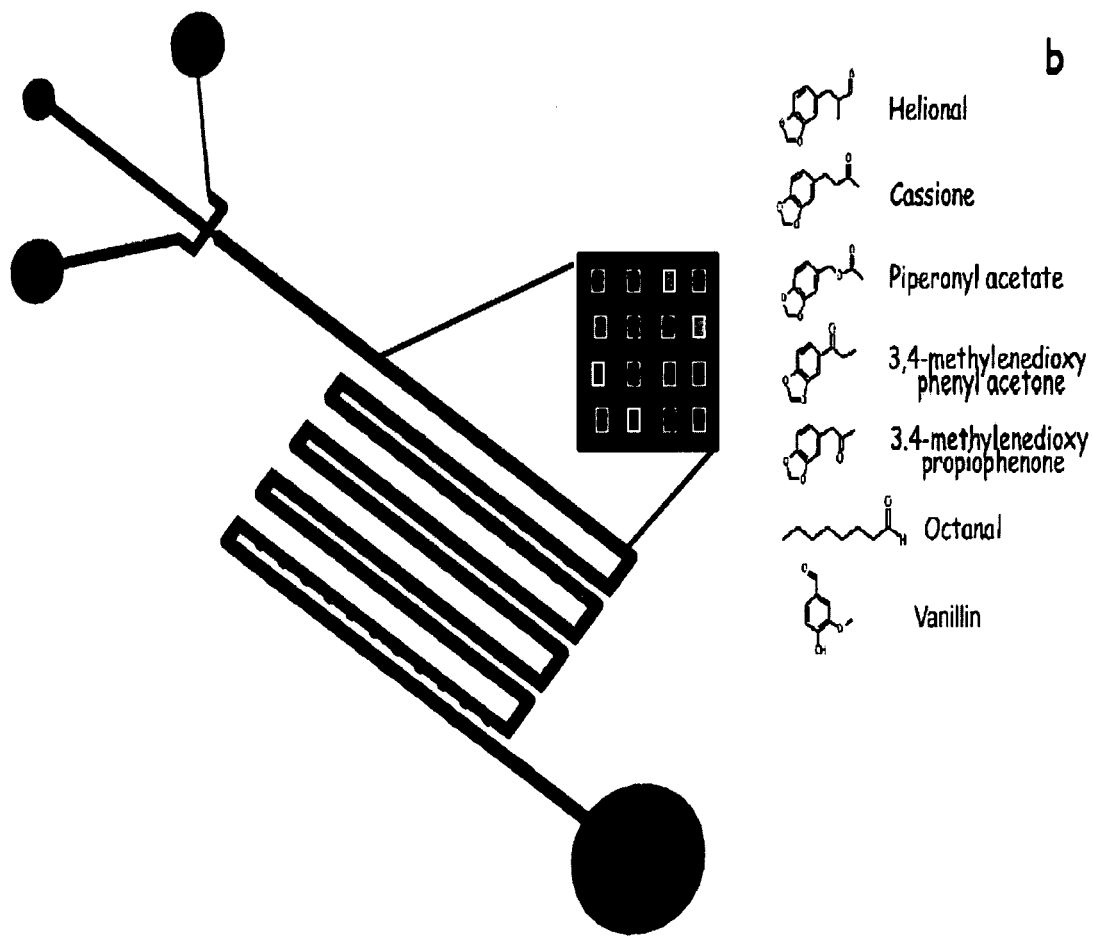
FIG. 12 represents an example of a bubble logic based gas detection schemes.

FIG. 12 represents an example of a bubble logic based gas detection schemes.

Data Processing

Evaluation of Data Using Biacore T100 Evaluation Software.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

EXAMPLE

Following the reports in the literature of producing GPCRs using *E. coli* extract, also for the lower price consideration of *E. coli* extract as compared to wheat germ based extract; we first used *E. coli* cell-free extracts from both Roche Diagnostics and Qiagen. However we found both produced hOR17-4 both soluble and insoluble at very low or non-detectable levels.

Since *E. coli* thioredoxin has been shown to greatly enhance the levels of GPCRs in *E. coli* based extracts, hOR17-4 was cloned into a plasmid including a thioredoxin N-terminally of hOR17-4. The addition of thioredoxin did however not affect the production yield of hOR17-4. The production is driven by a T7-promotor and any vector carrying a T7-promotor and termination sequence and ribosomal binding site should suffice for hOR17-4. Roche Diagnostics provides optimized vectors and linear generation template kits for high-yield production. When production was performed using a linear template, the production levels were not improved.

For production in wheat germ extract the hOR17-4 gene was cloned into pVEX1.3 and pVEX1.4 including a 6-residue histidine tag at either C- or N-terminal, respectively. Compared to production in *E. coli*, wheat germ lysate produced the olfactory receptor in detectable amounts. In addition, pilot studies showed that production from pVEX1.3 was far superior to pVEX1.4 (results not shown).

Effect of Detergents for Olfactory Receptor Yield and Solubility.

Detergents are a prerequisite when working with membrane proteins in solution, and this also holds true for membrane proteins produced in cell-free extracts since both *E. coli* and wheat germ extracts are devoid of lipids. We therefore carefully studied the optimal types and concentrations of various detergents in the cell-free system. A panel of eight detergents was chosen based on their efficacy in previous studies of GPCR production in cell-free extracts or on their ability to solubilize GPCRs expressed in vivo. The detergents were all tested at concentrations above their respective critical micelle concentration (CMC) value measured by the suppliers. The detergents effect on the amount of soluble and insoluble produced hOR17-4 was quantitatively measured using the dot blot method. OG, DDM, Cymal5 and Brij58 all reduced the production level and Anzergent3-14, FC14 and the Tri-mix either did not or only marginally affected the production level. Digitonin was found to be very effective in maintaining the protein soluble, with no insoluble protein detected. This is in agreement with previous studies of other GPCRs produced in *E. coli* based systems (20).

To avoid large protein-detergent micelles and to avoid inhibiting the production system at high concentrations of detergents, we systematically optimized detergent concentration from either decreasing or increasing its concentrations. Increasing the digitonin concentration resulted in very low levels of insoluble protein. In addition to digitonin, the optimal concentration of FC14 and the Tri-mix was also evaluated by increasing the concentration, since the productions levels were reasonable, but the protein was not completely soluble. The yield of soluble receptor could not be increased from increasing concentrations of FC14 or Tri-mix. This is most likely due to an inhibitory effect of these detergents on the cell-free production system. The most favorable digitonin concentration was found to be 0.2% and consequently chosen as the standard concentration.

To test whether the identified production conditions would also be suitable for other olfactory receptors, mouse receptors mOR23 and mS51 were also produced. The initial detergent screen was reduced to three detergents, namely FC14, Brij58 and the Tri-mix, mainly chosen for their efficacy in producing soluble hOR17-4. Production of soluble mOR23 was similar to the production of hOR17-4, with the highest yield in digitonin, but at a slightly higher digitonin concentration: 0.6%. The mS51 on the other hand was not produced at all in digitonin, but Brij58 at 0.1% and the Tri-mix at 1× produced high levels of soluble protein. Once the detergent composition was optimized, production in cell-free extract was proven to be very efficient in producing soluble olfactory receptors, as well as time saving compared to other production systems.

Optimizing buffer conditions. Using GFP as a reporter in SEC based buffer optimization is straightforward and time saving. Protein purification is not necessary and detection can be carried out on-line using a chromatography system (25). However, one drawback using GFP-fusions is that it has to be cleaved off for down-stream applications, such as crystallization. This process has to be optimized so as to avoid loss of protein activity and protein yield. We thus used an alternative approach where a sample from each SEC fraction was dot-blotted on a membrane and developed using an antibody directed against a short C-terminal tag. By using a short SEC column with only a 3-ml bed volume, up to 12 runs with different buffers could be performed in a single day. This time saving step allowed us to investigate the effect of 12 different detergents, 6 different concentrations of NaCl, 2 pH points and the presence of a reducing agent at 3 different concentrations.

Initially, the presence of 10 different detergents (Table 1) in the run was evaluated. Immediately after cell-free production the protein was captured on 1D4 coated beads and the new buffer was introduced during the washing step. The beads were washed with 100-bed volumes for complete detergent exchange. Exchange to buffers containing $C_8E_4$, DDOMG, LDAO or no detergent resulted in very low or non-detectable levels of hOR17-4 in the eluate from the beads, possibly due to receptor aggregation on the beads. The Tri-mix, Cyclophos5 and DDM on the other hand resulted in high yields, but the receptor eluted from the SEC with the void, indicating that the protein had aggregated to complexes larger than 600 kDa, which is the exclusion volume of the SEC column. Three of the detergents, Anzergent3-14, Brij58 and FC14, resulted in protein eluting as monomers or as higher molecular-weight oligomers. The receptor in FC14 buffer eluted at 1.71 ml, corresponding to 114 kDa. The amount of FC14 that binds to hOR17-4 molecule has been calculated to be 76 kDa and when added to the molecular weight of the receptor (36 kDa), it is very close to the observed molecular weight of 112 kDa. The buffers including the 3 most promising detergents were further optimized by varying the pH (pH 7.5 and pH 9.5), NaCl concentration (150 mM and 300 mM) and the presence of a reducing agent TCEP (0 mM and 1.5 mM).

The elution profiles from SEC in the buffers containing Anzergent3-14 and Brij58 respectively were not affected by the different salt concentrations, pH and reducing agent; the receptor was eluted as larger aggregates/oligomeric forms. In the case of FC14 detergent containing buffers there was a marked difference between the buffers. Higher pH decreased the monomer: aggregate ratio, higher salt concentration increased the same ratio. TCEP fully prevented aggregation and as indicated by the Gaussian shaped peak from SEC, the eluted protein is monodisperse. Addition of TCEP also resulted in a more pure sample from affinity purification. As a consequence, FC14 was chosen as detergent for further studies.

As high salt and detergent concentration could be detrimental for crystallization and because high concentration of reducing agent could hamper protein activity, a careful screening of those variables was performed to find the lowest concentration that still kept the protein in a monodispersed form. Increasing detergent concentration, up to 200×CMC, resulted in faster elution; 1.56 ml compared to 1.71 ml. This corresponds to a difference in calculated molecular weight of 100 kDa indicating resulting in a lower protein: detergent ratio at 200×CMC compared to 3×CMC. High protein: detergent ratio has been reported to impede crystallization and protein activity. Three×CMC resulted in the most well-defined peaks. The salt concentration was screened between 50 mM and 300 mM NaCl and concentrations below 150 mM were found with lower yields of receptor. Interestingly, varying salt concentration did not affect the receptor retention volume. Addition of reducing agent prevented aggregation at as low as 1 mM. The optimal buffer conditions were finally identified after testing different combinations of the salt, detergent and TCEP concentrations identified above. Two buffers, one with TCEP and one without, were chosen for further studies. Buffer 1: 25 mM Tris pH 7, 10% glycerol, 3×CMC FC14 and 200 mM NaCl and buffer 2: 25 mM Tris pH 7, 10% glycerol, 3×CMC FC14, 150 mM NaCl and 1 mM TCEP. SEC in a TCEP containing buffer resulted in a single Gaussian shaped peaks, indicative of a mono-dispersed protein sample. SEC without TCEP resulted in monomer, dimer as well as aggregation peaks but monomers could be separated from the other forms. Models of hOR17-4 predict the presence of disulphide bonds and their reduction by TCEP could hinder protein folding and function. TCEP however, breaks down over time and disulphide bonds will form again.

Large-scale purification. For further studies of secondary and tertiary structure as well as crystallization studies pure receptor at high concentration is needed. Crystallization is usually required at concentration greater than 5 mg/ml and circular dichroism measurements require concentrations ~0.2 mg/ml. Large-scale purification of the hOR17-4 receptor from up to 6 ml reaction solution was carried out by increasing the bed volume of 1D4 antibody coated beads. The same pattern as in the buffer optimization experiments was observed with TCEP resulting in a purer sample. The 1D4 antibody is highly specific and in comparison with a $Ni^{2+}$-chelate based affinity purification the 1D4 was able to purify the receptor from very low levels in the reaction solution to 70% purity in one step (results not shown). For further purification the eluted fractions were concentrated and applied to a 24 ml SEC column. The peaks containing hOR17-4 were pooled and concentrated again. The yield was determined to be ~0.3 mg pure hOR17-4/ml cell-free reaction solution. Eleven GPCRs have previously been produced in cell-free lysates at high levels. The yield of unpurified receptors ranged between 0.15-6 mg/ml reaction lysate (20, 21). A few of the receptors have been purified but no yields have been reported. Each purification step always results in protein loss, for example, a 50% yield has been reported for a 2-step purification scheme of the GPCR neurotensin (26). The yield of pure hOR17-4 is well in agreement with what could be expected from the literature of unpurified GPCRs produced in cell-free systems.

Secondary structure analysis of purified receptors. Correct protein structural folding largely depends on the mode of production and on the properties of the buffer milieu in which the protein is stored. Olfactory receptors are one member of the GPCRs, which are predicted to have mostly alpha-helical structure with seven trans-membrane helices. The GPCR alpha helical feature has been verified by the two high resolution structures that has been solved (27-29). Both CD spectra from purified hOR17-4 in buffer with and without reducing agent (buffer 1 and buffer 2) display the typical alpha helical features. The mean residue ellipticity was more distinct from hOR17-4 purified in buffer 2 that contains the reducing agent TCEP.

Surface plasmon resonance (Biacore A100) detection of odorant interaction with hOR17-4. The CD measurements suggest that hOR17-4 is correctly folded. We ask whether the receptor is able to bind to the odorants. The activity of a solubilized olfactory receptor is very difficult to assess since its ligands are mostly below 300 Da, the receptor itself is more than 100 times larger 36,000 Da. Furthermore the ligand binding pocket is predicted to be buried within the protein, which makes difficult to measure odorant binding.

Our experiments of odorant binding to the cells expressing odorant receptors showed binding responses. We therefore decided to use SPR to measure the binding of odorants to the hOR17-4 receptor. SPR is a label free technology, sensitive enough to detect the extremely small difference in mass when the odorant binds to the receptor captured on the sensor chip surface. Other in vivo experiments have shown that odorant lilial is a known agonists to hOR17-4 (30). We demonstrate the dose response binding in binding (RU) of lilial, which is a known agonist to hOR17-4 from in vivo studies to the hOR17-4 receptor on the Biacore chip. The binding response increases by increasing odorant concentration as expected. However, at concentration above 10 µM the response does not reach equilibrium indicating that the odorant start to fall out of solution.

The affinity constant of lillial binding to hOR17-4 have been reported to be in the micromolar range in vivo (30). However, the exact binding constant could not be precisely determined because of the very low lillial solubility at high concentrations. However, it could only approximately estimated to be within micromolar range which is in agreement with the in vivo observation. Additional experiments using more water-soluble odorants may address this question.

CONCLUSION

Our study of producing three olfactory receptors using wheat germ cell-free extracts proved the simple technology to be very useful to obtain functional GPCR membrane proteins. Together with efficient buffer scouting using small volume size exclusion chromatography, appropriate detergent and other buffer components could be identified. In addition, the high-yield production provided enough olfactory receptor to initiate detail structural analysis.

Since most membrane proteins are natural molecular devices, our work will likely facilitate the design of membrane protein based nano-bio devices for a wide range of applications, from detection of extremely infinitesimal amounts of odorants, emitted from diverse diseases and environment, to direct harvest of solar energy.

Materials and Methods
Reagents.

All detergents where purchased from Anatrace, Maumee, Ohio, US exempt Digitonin EMD (Merck), Darmstadt, Germany. The cell-free protein production kits (both E. coli and wheat germ systems) were purchased from Roche Diagnostics, Indianapolis, Ind., USA. Protein purification materials are purchased from GE Healthcare Life Science, Uppsala, Sweden. Others are described below.

Cell-Free Production.

Generation of DNA template. The open reading frame for the human olfactory receptor 17-4 (hOR17-4) (UniProt accession number P34982) was generated using PCR-based gene synthesis. By using the free program DNAWorks (http:helixweb.nih.gov/dnaworks) oligonucleotides were designed to build the open reading frames of the olfactory receptors for PCR-based gene synthesis. The open reading frame of hOR17-4 was optimized for E. coli class II codon usage with the addition of a six residue long C-terminal histidine tag followed by a stop codon and N and C-terminal att-sites. The following parameters were used for automatic design of the oligos: oligo size 45 nucleotides, annealing temperature 58° C., 25 nM oligonucleotide, 10 mM sodium, 2.0 mM $Mg^{2+}$ and the codon frequency threshold was set at 100%. The PCR product was cloned into pDEST42 and pBAD-DEST49 (Invitrogen Carlsbad, Calif., USA) for non-fused and thioredoxin-fused protein production, respectively, according to manufacturer's instructions. Linear templates for production in RTS 100 HY E. coli kit was generated using RTS E. coli Linear Template Generation Set (Roche), according manufacturer's instructions with a six residue long C-terminal histidine tag. For production of hOR17-4, OR23 and S51 in wheat germ extract a human codon optimized version was produced in a similar manner but with Nco I and Sma I restriction sites for cloning into pIVEX1.3 WG and pVEX1.4 WG which includes a six residue long C- or N-terminal histidine tag, respectively, according to manufacturer's instructions. A third construct for production in wheat germ extract was generated with the nine residues long Rho-tag (TETSQVAPA) instead of the C-terminal histidine tag. The constructs encoding the olfactory receptors were verified by DNA sequencing. Plasmid DNA template for cell-free production was obtained from Genopure Maxi Kit (Roche) with an OD260/280<1.7. The plasmid was aliquoted and stored at −20° C. and the same batch was used throughout the study.

Cell-Free Production in *Escherichia coli* Extracts.

Production of hOR17-4 in E. coli extracts was performed using RTS 100 HY E. coli kit, RTS E. coli Disulphide kit, and EasyXpress Protein Synthesis Mini Kit (Qiagen, Valencia, Calif., USA) according to manufacturer's instructions in pDEST42 and pBAD-DEST49 production plasmids. A linear template was also used in the case of the RTS 100 HY E. coli kit.

Cell-Free Production in Wheat Germ Extracts.

Small-scale production in wheat germ lysate was performed in 50 µl reaction chambers using RTS 100 Wheat Germ CECF kit. Large scale 1 ml reactions, was carried out using RTS 500 Wheat Germ CECF kit.

An initial screen was set up to test the effect of detergents on the yield of soluble receptor hOR17-4 by adding different detergents to the reaction chambers, see Table 1. The concentrations tested were all above the CMC of the respective detergent. The concentrations of respectively Digitonin, Brij58, DDM, OG and DDM were based on previous results of production of GPCRs in E. coli cell-free systems (20). The optimal concentration of FC14, Digitonin and the Tri-mix to keep the freshly produced receptor soluble was further tested at concentrations between 0.014-0.055%, 0.2-0.6% and 1-3×, respectively. Initial detergent screening for soluble production of OR23 and S51 was performed in FC14, Digitonin and the Tri-mix and the optimal concentration was identified by titration of the detergent that resulted in the highest production in the initial screen with hOR17-4. When the production cycle had terminated the reaction solution was centrifuged for ten minutes at 16,000×g at four degrees Celsius to separate soluble and insoluble proteins.

To analyze the effect of the different detergents 1.5 µl of the soluble and insoluble fraction was dotted on a Protran BA85 nitrocellulose membrane (Whatman, Dassel, Germany). The membrane was blocked, washed, and probed with either a 1D4 antibody directed against the Rho-tag or an anti-His antibody (Novagen/Merck, Darmstadt, Germany), and developed as previously described (31). The intensity of the spot was recorded using an AlphaImager (Alpha Innotech, San Leandro, Calif., US).

Olfactory Receptor Purification.

Purification of the receptor was carried out using Sepharose-4B beads (GE Healthcare, Uppsala, Sweden) with covalently linked 1D4 antibodies specific for the Rho-tag. The antibody coated beads were prepared as described earlier (32). For small scale purification from 75 µl production reaction solution 50 µl beads washed in PBS was used. The reaction solution-bead mix was incubated end over end for four hours at 4° C. Purification was hereafter performed in empty spin columns and unbound material was removed by gravity flow. The beads were washed five times using in total five ml of purification buffer. Finally, hOR17-4 was eluted by adding 50 µl purification buffer containing 200 µM of the peptide TETSQVAPA to the beads and the column was capped and incubated one hour at room temperature shaking. The protein was collected by centrifugation at 800×g for ten seconds.

Large scale purification was performed as described above with the following exceptions. The amount of 1D4 antibody coated beads was increased to a final 3:2 ratio of cell-free reaction solution to beads. The receptor was eluted in 5-7 bed volumes of buffer supplemented with the elution peptide. The eluted protein was concentrated to one third of the volume using a ten NMWL Microcon spin filter (Millipore, Billerica, Mass., USA) and injected on a Superdex 200 10/300 24 ml SEC column (GE Healthcare Life Science) for further purification and to remove elution peptide from the sample. For stabilization studies and crystallization the eluted receptor was concentrated using a ten NMWL Amicon Ultra-4 Centrifugal Filter (Millipore). Protein concentration was measured throughout the study by a reducing agent compatible microplate BCA assay (Pierce, Rockford, Ill., USA).

Optimization of Buffer Conditions.

After small scale affinity purification using 1D4-coupled beads the oligomeric state of the protein eluted in different buffers was assayed using a short three ml size exclusion column, Superdex 200 5/150GL (GE Healthcare Life Science). 50 μl fractions were collected in micro well plates and 1.5 μl of each fraction was dotted on a cellulose membrane (Protran BA85 nitrocellulose membrane) to assay protein amount. The intensity recorded from each spot was inserted in an activity histogram in the ÄKTA software Unicorn version 5.11 (GE Healthcare Life Science) and smoothed over two fraction volumes. For buffer optimization a one ml wheat germ reaction was used for scouting up to twelve buffers.

Secondary Structural Analysis Using Circular Dichroism.

CD measurements of the hOR17-4 were performed at protein at 0.3 mg/ml. The investigations were carried out on an Aviv 202 spectropolarimeter (Aviv Biomedical, Lakewood, N.J., USA) using a one mm path length cell, equilibrated at 25° C. Spectra were recorded between 200 and 250 nm with one nm resolution with a two second averaging time. The final spectra were baseline-corrected by subtracting the corresponding buffer spectra obtained under identical conditions. Results were expressed as the molar mean residue ellipticity (θ) at a given wavelength.

Surface Plasma Resonance (Biacore A100) Odorant Binding Assay.

All odorant binding experiments were performed on a Biacore™ A100 (GE Healthcare, Uppsala, Sweden) at 25° C. A Biacore™ A100 was used in the present studies since it has a parallel flow configuration thus allowing assay development e.g. solubilization conditions to be tested and optimized in parallel in a multiplexed format. The sensor chip CM4, amine coupling kit, HBS (10 mM Hepes, 0.15 M NaCl, pH 7.4) and PBS were from (GE Healthcare, Uppsala, Sweden).

The anti Rho-tag antibody 1D4 at 40 μg/ml in 10 mM sodium acetate pH 5.5 was immobilized onto a series S sensor chip using standard amine-coupling chemistry in HBS running buffer at 10 μl/min (33). The amount of coupled 1D4 was about 5500 RU. Control surfaces were prepared similarly without protein derivatization and utilized as a reference surfaces for compound binding experiments.

Cell-free lysate containing the expressed olfactory receptor was centrifuged for 15 at 14000×g at 4° C., to remove larger particles. The supernatant, containing about 0.6 mg/ml olfactory receptor, was immediately captured on the surface plasmon resonance (SPR) chip using PBS, 0.1% CHAPS, 0.02% CHS, 0.1% DDM and 1% (v/v) ethanol as running buffer at 10 μl/min. A four-minute injection resulted in a surface density of about 6000 RU.

Fresh odorant lilial solutions were made as follows. Pure odorant was diluted in ethanol to 0.5 M. This solution was diluted 67 times in PBS, 0.1% CHAPS, 0.02% CHS, 0.1% DDM to obtain a 7.5 mM odorant solution in running buffer with 1% (v/v) ethanol. Further dilutions were made in running buffer containing 1% (v/v) ethanol to obtain a concentration series of 5 μM, 10 μM, 20 μM and 40 μM of odorant lilial.

For the actual binding measurements, the odorant concentration series were injected from low to high concentration over control and derivatized surfaces for 30 seconds with a flow rate of 60 μl/min. Zero concentration blank buffer cycles were included as negative control samples. Solvent correction procedures were included to compensate for any DMSO related bulk refractive index variations and performed as described previously[34]. Non-specific binding effects to sensor surface CM4 were absent for all analyses reported.

Data analysis was carried out using Biacore A100 evaluation software. Data were prepared by subtraction of reference surface data and blank buffer sample data, a procedure commonly referred to as double referencing (35). Solvent correction was then applied as described previously (34).

REFERENCES

1. Wallin, E., von Heijne, G. (1998) Genome-wide analysis of integral membrane proteins from eubacterial, archaean, and eukaryotic organisms. Protein Sci 7: 1029-1038.
2. Loll, P. J. (2003) Membrane protein structural biology: the high throughput challenge. J Struct Biol 142: 144-153.
3. Nilsson, J., Persson, B., von Heijne, G. (2005) Comparative analysis of amino acid distributions in integral membrane proteins from 107 genomes. Proteins 60: 606-616.
4. Strader, C. D., Fong, T. M., Tota, M. R., Underwood, D., Dixon, R. A. (1994) Structure and function of G protein-coupled receptors. Annu Rev Biochem 63: 101-132.
5. Burne, H., Horuk, R., Kuhnke, J., Micheal, H. (2007) GPCRs: From deorphanization to lead structure identification (Spriner-Verlag, Berlin, Heidelberg, N.Y.).
6. Buck, L., Axel, R. (1991) A novel multigene family may encode odorant receptors: a molecular basis for odor recognition. Cell 65: 175-187.
7. Araneda, R. C., Kini, A. D., Firestein, S. (2000) The molecular receptive range of an odorant receptor. Nat Neurosci 3: 1248-1255.
8. Breer, H., Krieger, J., Meinken, C., Kiefer, H., Strotmann, J. (1998) Expression and functional analysis of olfactory receptors. Ann N Y Acad Sci 855: 175-181.
9. Kiefer, H., Krieger, J., Olszewski, J. D., Von Heijne, G., Prestwich, G. D., et al. (1996) Expression of an olfactory receptor in *Escherichia coli*: purification, reconstitution, and ligand binding. Biochemistry 35: 16077-16084.
10. Vidic, J. M., Grosclaude, J., Persuy, M. A., Aioun, J., Salesse, R., et al. (2006) Quantitative assessment of olfactory receptors activity in immobilized nanosomes: a novel concept for bioelectronic nose. Lab Chip 6: 1026-1032.
11. Ivic, L., Zhang, C., Zhang, X., Yoon, S. O., Firestein, S. (2002) Intracellular trafficking of a tagged and functional mammalian olfactory receptor. J Neurobiol 50: 56-68.

12. Lundstrom, K. (2004) Structural genomics on membrane proteins: mini review. Comb Chem High Throughput Screen 7: 431-439.
13. Tate, C. G. (2001) Overexpression of mammalian integral membrane proteins for structural studies. FEBS Lett 504: 94-98.
14. Wagner, S., Bader, M. L., Drew, D., de Gier, J. W. (2006) Rationalizing membrane protein overexpression. Trends Biotechnol 24: 364-371.
15. Buchner, J., Pastan, I., Brinkmann, U. (1992) A method for increasing the yield of properly folded recombinant fusion proteins: single-chain immunotoxins from renaturation of bacterial inclusion bodies. Anal Biochem 205: 263-270.
16. Spirin, A. S., Baranov, V. I., Ryabova, L. A., Ovodov, S. Y., Alakhov, Y. B. (1988) A continuous cell-free translation system capable of producing polypeptides in high yield. Science 242: 1162-1164.
17. Endo, Y., Sawasaki, T. (2006) Cell-free expression systems for eukaryotic protein production. Curr Opin Biotechnol 17: 373-380.
18. Yokoyama, S. (2003) Protein expression systems for structural genomics and proteomics. Curr Opin Chem Biol 7: 39-43.
19. Yokoyama, S., Terwilliger, T. C., Kuramitsu, S., Moras, D., Sussman, J. L. (2007) RIKEN aids international structural genomics efforts. Nature 445: 21.
20. Klammt, C., Schwarz, D., Fendler, K., Haase, W., Dotsch, V., et al. (2005) Evaluation of detergents for the soluble expression of alpha-helical and beta-barrel-type integral membrane proteins by a preparative scale individual cell-free expression system. FEBS J 272: 6024-6038.
21. Ishihara, G., Goto, M., Saeki, M., Ito, K., Hori, T., et al. (2005) Expression of G protein coupled receptors in a cell-free translational system using detergents and thioredoxin-fusion vectors. Protein Expr Purif 41: 27-37.
22. Columbus, L., Lipfert, J., Klock, H., Millett, I., Doniach, S., et al. (2006) Expression, purification, and characterization of Thermotoga maritima membrane proteins for structure determination. Protein Sci 15: 961-975.
23. Savage, D. F., Anderson, C. L., Robles-Colmenares, Y., Newby, Z. E., Stroud, R. M. (2007) Cell-free complements in vivo expression of the E. coli membrane proteome. Protein Sci 16: 966-976.
24. Jasti, J., Furukawa, H., Gonzales, E. B., Gouaux, E. (2007) Structure of acid-sensing ion channel 1 at 1.9 A resolution and low pH. Nature 449: 316-323.
25. Kawate, T., Gouaux, E. (2006) Fluorescence-detection size-exclusion chromatography for precrystallization screening of integral membrane proteins. Structure 14: 673-681.
26. Grisshammer, R., White, J. F., Trinh, L. B., Shiloach, J. (2005) Large-scale expression and purification of a G-protein-coupled receptor for structure determination—an overview. J Struct Funct Genomics 6: 159-163.
27. Cherezov, V., Rosenbaum, D. M., Hanson, M. A., Rasmussen, S. G., Thian, F. S., et al. (2007) High-resolution crystal structure of an engineered human beta2-adrenergic G protein-coupled receptor. Science 318: 1258-1265.
28. Rasmussen, S. G., Choi, H. J., Rosenbaum, D. M., Kobilka, T. S., Thian, F. S., et al. (2007) Crystal structure of the human beta2 adrenergic G-protein-coupled receptor. Nature 450: 383-387.
29. Rosenbaum, D. M., Cherezov, V., Hanson, M. A., Rasmussen, S. G., Thian, F. S., et al. (2007) GPCR engineering yields high-resolution structural insights into beta2-adrenergic receptor function. Science 318: 1266-1273.
30. Spehr, M., Gisselmann, G., Poplawski, A., Riffell, J. A., Wetzel, C. H., et al. (2003) Identification of a testicular odorant receptor mediating human sperm chemotaxis. Science 299: 2054-2058.
31. Reeves, P. J., Callewaert, N., Contreras, R., Khorana, H. G. (2002) Structure and function in rhodopsin: high-level expression of rhodopsin with restricted and homogeneous N-glycosylation by a tetracycline-inducible N-acetylglucosaminyltransferase I-negative HEK293S stable mammalian cell line. Proc Natl Acad Sci USA 99: 13419-13424.
32. Oprian, D. D., Molday, R. S., Kaufman, R. J., Khorana, H. G. (1987) Expression of a synthetic bovine rhodopsin gene in monkey kidney cells. Proc Natl Acad Sci USA 84: 8874-8878.
33. Biacore (2003) Biacore sensor surface handbook (Biacore Uppsala, Sweden).
34. Karlsson, R., Kullman-Magnusson, M., Hamalainen, M. D., Remaeus, A., Andersson, K., et al. (2000) Biosensor analysis of drug-target interactions: direct and competitive binding assays for investigation of interactions between thrombin and thrombin inhibitors. Anal Biochem 278: 1-13.
35. Myszka, D. G. (1999) Improving biosensor analysis. J Mol Recognit 12: 279-284.

The articles cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A bio-sensing nanodevice comprising: a stabilized biologically-derived G-protein coupled olfactory receptor-immobilized on a support, a real time receptor-ligand binding detection system method, a test composition delivery system and a test composition recognition program, wherein the stabilized receptor is stabilized with surfactant peptides selected from the group consisting of:

| Sequence (N → C) | Formula |
|---|---|
| $(\Phi)_m(+)_n$ | 1 |
| $(+)_n(\Phi)_m$ | 2 |
| $(\Phi)_m(-)_n$ | 3 |
| $(-)_n(\Phi)_m$ | 4 |
| $(-)_n(\Phi)_m(-)_n$ | 5 |
| $(+)_n(\Phi)_m(+)_n$ | 6 |
| $(\Phi)_m(-)n(\Phi)_m$ | 7 |
| $(\Phi)_m(+)n(\Phi)_m$ | 8 |
| $(+)_n(\Phi)_m(-)_n$ | 9 |
| $(-)_n(\Phi)_m(+)_n$ | 10 | wherein:
($\Phi$) represents independently for each occurrence a natural or non-natural amino acid comprising a hydrophobic sidechain;
(+) represents independently for each occurrence a natural or non-natural amino acid comprising a sidechain that is cationic at physiological pH;
(−) represents independently for each occurrence a natural or non-natural amino acid comprising a sidechain that is anionic at physiological pH;
wherein the terminal amino acids are optionally substituted;
m for each occurrence represents an integer greater than or equal to 5; and
n for each occurrence represents an integer greater than or equal to 1;
wherein the test composition delivery system is a microfluidic bubble logic operation.

2. The bio-sensing nanodevice of claim 1, wherein the microfluidic bubble logic operation comprises microfluidic channels adapted for receiving micron-sized droplets and bubbles comprising a test composition.

* * * * *

SEQUENCE LISTING

```
<160> NUMBER OF SEQ ID NOS: 43

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide Surfactant

<400> SEQUENCE: 1

Ala Ala Ala Ala Ala Ala Asp
 1               5
```

```
<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide Surfactant

<400> SEQUENCE: 2

Val Val Val Val Val Val Asp
 1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide Surfactant

<400> SEQUENCE: 3

Ala Ala Ala Ala Ala Ala Asp Asp
 1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide Surfactant

<400> SEQUENCE: 4

Val Val Val Val Val Val Asp Asp
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide Surfactant

<400> SEQUENCE: 5

Leu Leu Leu Leu Leu Leu Asp Asp
 1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide Surfactant

<400> SEQUENCE: 6

Lys Lys Ile Ile Ile Ile Ile Ile
 1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide Surfactant

<400> SEQUENCE: 7

Lys Lys Leu Leu Leu Leu Leu Leu
 1               5
```

-continued

```
<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide Surfactant

<400> SEQUENCE: 8

Lys Lys Ala Ala Ala Ala Ala Ala Ala
 1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide Surfactant

<400> SEQUENCE: 9

Lys Lys Val Val Val Val Val Val
 1               5

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 10

Asp Asp Asp Asp Asp Asp Asp Asp Asp Asp Ala Ala Ala Ala Ala Ala
 1               5                  10                  15

Ala Ala Ala Ala
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 11

Ala Ala Ala Ala Ala Ala Ala Ala Ala Ala Asp Asp Asp Asp Asp Asp
 1               5                  10                  15

Asp Asp Asp Asp
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 12

Glu Glu Glu Glu Glu Glu Glu Glu Glu Glu Ala Ala Ala Ala Ala Ala
 1               5                  10                  15

Ala Ala Ala Ala
            20

<210> SEQ ID NO 13
<211> LENGTH: 20
<212> TYPE: PRT
<213> ORGANISM: Artificial Sequence
```

```
<220> FEATURE:
<223> OTHER INFORMATION: Synthetic Peptide Surfactant

<400> SEQUENCE: 13

Ala Ala Ala Ala Ala Ala Ala Ala Ala Glu Glu Glu Glu Glu Glu
1               5                   10                  15

Glu Glu Glu Glu
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 14

Asp Asp Asp Asp Asp Asp Asp Asp Asp Val Val Val Val Val Val
1               5                   10                  15

Val Val Val Val
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 15

Val Val Val Val Val Val Val Val Val Asp Asp Asp Asp Asp Asp
1               5                   10                  15

Asp Asp Asp Asp
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 16

Asp Asp Asp Asp Asp Asp Asp Asp Asp Asp Pro Pro Pro Pro Pro
1               5                   10                  15

Pro Pro Pro Pro
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 17

Pro Pro Pro Pro Pro Pro Pro Pro Pro Asp Asp Asp Asp Asp Asp
1               5                   10                  15

Asp Asp Asp Asp
            20

<210> SEQ ID NO 18
<211> LENGTH: 20
<212> TYPE: PRT
```

```
<213> ORGANISM: Artificial Sequence
<220> FEATURE:
<223> OTHER INFORMATION: Synthetic Peptide Surfactant

<400> SEQUENCE: 18

Ala Ala Ala Ala Ala Ala Ala Ala Ala Ala His His His His His His
1               5                   10                  15

His His His His
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 19

His His His His His His His His His His Ala Ala Ala Ala Ala Ala
1               5                   10                  15

Ala Ala Ala Ala
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 20

Lys Lys Lys Lys Lys Lys Lys Lys Lys Lys Ala Ala Ala Ala Ala Ala
1               5                   10                  15

Ala Ala Ala Ala
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 21

Ala Ala Ala Ala Ala Ala Ala Ala Ala Ala Lys Lys Lys Lys Lys Lys
1               5                   10                  15

Lys Lys Lys Lys
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic Peptide Surfactant

<400> SEQUENCE: 22

Arg Arg Arg Arg Arg Arg Arg Arg Arg Arg Ala Ala Ala Ala Ala Ala
1               5                   10                  15

Ala Ala Ala Ala
            20

<210> SEQ ID NO 23
<211> LENGTH: 20
```

```
<212> TYPE: PRT
<213> ORGANISM: Artificial Sequence
<220> FEATURE:
<223> OTHER INFORMATION: Synthetic Peptide Surfactant

<400> SEQUENCE: 23

Ala Ala Ala Ala Ala Ala Ala Ala Ala Arg Arg Arg Arg Arg
 1               5                  10                  15

Arg Arg Arg Arg
            20

<210> SEQ ID NO 24
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 24

Asp Asp Asp Asp Asp Asp Asp Asp Asp Asp Ala Ala Ala Ala Ala
 1               5                  10                  15

Ala Ala Ala Ala Asp Asp Asp Asp Asp Asp Asp Asp Asp Asp
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 25

Glu Glu Glu Glu Glu Glu Glu Glu Glu Glu Ala Ala Ala Ala Ala
 1               5                  10                  15

Ala Ala Ala Ala Glu Glu Glu Glu Glu Glu Glu Glu Glu Glu
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 26

Asp Asp Asp Asp Asp Asp Asp Asp Asp Asp Val Val Val Val Val
 1               5                  10                  15

Val Val Val Val Asp Asp Asp Asp Asp Asp Asp Asp Asp Asp
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 27

Asp Asp Asp Asp Asp Asp Asp Asp Asp Asp Pro Pro Pro Pro Pro
 1               5                  10                  15

Pro Pro Pro Pro Asp Asp Asp Asp Asp Asp Asp Asp Asp Asp
            20                  25                  30

<210> SEQ ID NO 28
```

```
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 28

His His His His His His His His His Ala Ala Ala Ala Ala Ala
1               5                   10                  15

Ala Ala Ala Ala His His His His His His His His His
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 29

Lys Lys Lys Lys Lys Lys Lys Lys Lys Lys Ala Ala Ala Ala Ala
1               5                   10                  15

Ala Ala Ala Ala Lys Lys Lys Lys Lys Lys Lys Lys Lys Lys
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 30

Arg Arg Arg Arg Arg Arg Arg Arg Arg Arg Ala Ala Ala Ala Ala
1               5                   10                  15

Ala Ala Ala Ala Arg Arg Arg Arg Arg Arg Arg Arg Arg Arg
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 31

Ala Ala Ala Ala Ala Ala Ala Ala Ala Ala Asp Asp Asp Asp Asp
1               5                   10                  15

Asp Asp Asp Asp Ala Ala Ala Ala Ala Ala Ala Ala Ala Ala
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 32

Ala Ala Ala Ala Ala Ala Ala Ala Ala Ala Glu Glu Glu Glu Glu
1               5                   10                  15

Glu Glu Glu Glu Ala Ala Ala Ala Ala Ala Ala Ala Ala Ala
            20                  25                  30
```

-continued

```
<210> SEQ ID NO 33
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 33

Val Val Val Val Val Val Val Val Asp Asp Asp Asp Asp Asp Asp Asp
1               5                   10                  15

Asp Asp Asp Asp Val Val Val Val Val Val Val Val Val Val
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 34

Pro Pro Pro Pro Pro Pro Pro Pro Asp Asp Asp Asp Asp Asp Asp
1               5                   10                  15

Asp Asp Asp Asp Pro Pro Pro Pro Pro Pro Pro Pro
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 35

Ala Ala Ala Ala Ala Ala Ala Ala Ala His His His His His His
1               5                   10                  15

His His His His Ala Ala Ala Ala Ala Ala Ala Ala Ala
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 36

Ala Ala Ala Ala Ala Ala Ala Ala Ala Lys Lys Lys Lys Lys Lys
1               5                   10                  15

Lys Lys Lys Lys Ala Ala Ala Ala Ala Ala Ala Ala Ala
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 37

Ala Ala Ala Ala Ala Ala Ala Ala Ala Arg Arg Arg Arg Arg Arg
1               5                   10                  15

Arg Arg Arg Arg Ala Ala Ala Ala Ala Ala Ala Ala Ala
            20                  25                  30
```

```
<210> SEQ ID NO 38
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 38

Lys Lys Lys Lys Lys Lys Lys Lys Lys Lys Ala Ala Ala Ala Ala
1               5                   10                  15

Ala Ala Ala Ala Asp Asp Asp Asp Asp Asp Asp Asp Asp Asp
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 39

Lys Lys Lys Lys Lys Lys Lys Lys Lys Lys Ala Ala Ala Ala Ala
1               5                   10                  15

Ala Ala Ala Ala Glu Glu Glu Glu Glu Glu Glu Glu Glu Glu
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 40

Arg Arg Arg Arg Arg Arg Arg Arg Arg Arg Val Val Val Val Val
1               5                   10                  15

Val Val Val Val Asp Asp Asp Asp Asp Asp Asp Asp Asp Asp
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 41

Lys Lys Lys Lys Lys Lys Lys Lys Lys Lys Pro Pro Pro Pro Pro
1               5                   10                  15

Pro Pro Pro Pro Asp Asp Asp Asp Asp Asp Asp Asp Asp Asp
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Synthetic Peptide Surfactant

<400> SEQUENCE: 42

His His His His His His His His His His Ala Ala Ala Ala Ala
1               5                   10                  15

Ala Ala Ala Ala Glu Glu Glu Glu Glu Glu Glu Glu Glu Glu
            20                  25                  30
```

```
<210> SEQ ID NO 43
<211> LENGTH: 7
<212> TYPE: PRT
<213> ORGANISM: Artificial Sequence
<220> FEATURE:
<223> OTHER INFORMATION: Synthetic Peptide Surfactant

<400> SEQUENCE: 43

Ala Ala Ala Ala Ala Ala Lys
 1               5
```